United States Patent
Berger et al.

(10) Patent No.: US 7,365,197 B2
(45) Date of Patent: Apr. 29, 2008

(54) METHOD FOR THE REGIOSELECTIVE PREPARATION OF SUBSTITUTED BENZO[G]QUINOLINE-3-CARBONITRILES AND BENZO[G]QUINAZOLINES

(75) Inventors: Dan Maarten Berger, New City, NY (US); Gary Harold Birnberg, Tuxedo Park, NY (US); Yanong Wang, Nanuet, NY (US)

(73) Assignee: Wyeth, Madison, NJ (US)

( * ) Notice: Subject to any disclaimer, the term of this patent is extended or adjusted under 35 U.S.C. 154(b) by 818 days.

(21) Appl. No.: 10/250,376

(22) PCT Filed: Dec. 11, 2001

(86) PCT No.: PCT/US01/47939

§ 371 (c)(1),
(2), (4) Date: Oct. 23, 2003

(87) PCT Pub. No.: WO02/053528

PCT Pub. Date: Jul. 11, 2002

(65) Prior Publication Data

US 2006/0041127 A1 Feb. 23, 2006

Related U.S. Application Data

(60) Provisional application No. 60/259,190, filed on Dec. 29, 2000.

(51) Int. Cl.
*C07D 265/30* (2006.01)
*C07D 295/12* (2006.01)
*C07D 295/22* (2006.01)
*C07D 255/00* (2006.01)
*C07C 229/00* (2006.01)

(52) U.S. Cl. .................. 544/166; 560/19; 560/45; 558/418

(58) Field of Classification Search .............. None
See application file for complete search history.

(56) References Cited

U.S. PATENT DOCUMENTS 5,679,683 A    10/1997  Bridges et al. ............. 514/267
2002/0091273 A1*  7/2002  Berger et al. ................. 549/74

FOREIGN PATENT DOCUMENTS

| WO | 95/19970 | 7/1995 |
| WO | 97/13760 | 4/1997 |
| WO | 97/49688 | 12/1997 |
| WO | WO-A-98 43960 | 10/1998 |
| WO | 00/68201 | 11/2000 |
| WO | WO-A-01 47892 | 7/2001 |

OTHER PUBLICATIONS

Kobayashi, et al., New General Synthesis of tert-Butyl 3-Amino-2-naphthalenecarboxylates by an Electrocyclic Reaction of o-Quinonedimethides generated from tert-Butyl (Z)-3-Amino-3-(bicycle[4.2.0]octa-1,3,5-trien-7-yl)prop-2-enoates, J. Chem. Soc., Chem. Commun., 780-81 (1992).*

Rewcastle et al., "Tyrosine Kinase Inhibitors. 9. Synthesis and Evaluation of Fused Tricyclic Quinazoline Analogues as ATP Site Inhibitors of the Tyrosine Kinase Activity of the Epidermal Growth Factor Receptor," J. Med. Chem. 39:918-928 (1996).

* cited by examiner

*Primary Examiner*—James O. Wilson
*Assistant Examiner*—Erich Leeser
(74) *Attorney, Agent, or Firm*—David A. Rubin; Anne M. Rosenblum

(57) ABSTRACT

This invention relates to a method for the regioselective synthesis of 4,6,7,8-substituted benzo[g]quinoline-3-carbonitriles and 4,6,7,8-substituted benzo[g]quinazolines as well as intermediates thereof. The compounds derived from this invention are useful for the treatment of a variety of diseases that are a result of deregulation of these PTK's, and more specifically, are anti-cancer agents and are useful for the treatment of cancer in mammals. In addition, the compounds derived from this invention are useful for the treatment of polycystic kidney disease in mammals.

7 Claims, No Drawings

METHOD FOR THE REGIOSELECTIVE PREPARATION OF SUBSTITUTED BENZO[G]QUINOLINE-3-CARBONITRILES AND BENZO[G]QUINAZOLINES

This application under 35 U.S.C. § 371(c) is based on International Application No. PCT/US01/47939, filed on Dec. 11, 2001 and claims priority under 35 U.S.C. § 119(e) of U.S. Provisional Application No. 60/259,190 filed on Dec. 29, 2000, abandoned, the entire disclosure of which is hereby incorporated by reference.

FIELD OF THE INVENTION

This invention relates to a method for the regioselective synthesis of 4,6,7,8-substituted benzo[g]quinoline-3-carbonitriles and 4,6,7,8-substituted benzo[g]quinazolines as well as intermediates thereof. The compounds derived from this invention are useful for the treatment of a variety of diseases that are a result of deregulation of these PTK's, and more specifically, are anti-cancer agents and are useful for the treatment of cancer in mammals. In addition, the compounds derived from this invention are useful for the treatment of polycystic kidney disease in mammals.

BACKGROUND OF THE INVENTION

Certain 4-anilino-benzo[g]quinoline-3-carbonitriles as protein kinase inhibitors are disclosed in PCT patent application WO0147892.

Certain 4-anilino-benzo[g]quinazolines as protein kinase inhibitors are disclosed in several patents and publications: WO9749688, U.S. Pat. No. 5,679,683, WO9519970, WO9713760 and J. Med. Chem. 1996, 39, 918-928. These references disclose that 4-anilino-benzo[g]quinazolines and 4-anilin-benzo[g]quinoline-3-carbonitriles possess potent activity as protein kinase inhibitors.

Throughout this patent application, the benzo[g]quinoline ring system will be numbered as indicated in the formula below:

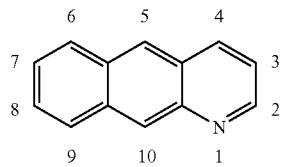

Throughout this patent application, the benzo[g]quinazoline ring system will be numbered as indicated in the formula below:

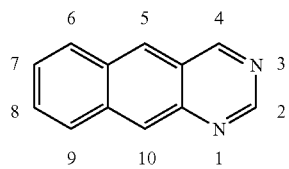

SUMMARY OF THE INVENTION

The present invention relates to a process for the production of 6,7,8-substituted 3-amino-2-naphthoates or 3-amino-2-naphthonitriles of formula (A)

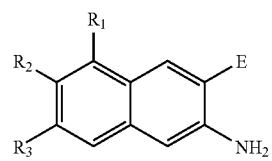

wherein
E is cyano or E is an alkoxycarbonyl of 2-12 carbons, —$CO_2$-Ph, —$CO_2$-L, cycloalkoxycarbonyl of 4-12 carbons, alkenyloxycarbonyl of 3-12 carbons, cycloalkenyloxycarbonyl of 5-12 carbons, alkynyloxycarbonyl of 4-12 carbons, which may be optionally substituted on a carbon atom with one or more $R_6$ groups;

$R_1$, $R_2$ and $R_3$ are each, independently, hydrogen, halogen, hydroxy, amino, hydroxyamino, trifluoromethyl, trifluoromethoxy, mercapto, alkyl of 1-6 carbon atoms, cycloalkyl of 3-8 carbon atoms, alkenyl of 2-6 carbon atoms, alkynyl of 2-6 carbon atoms, alkenyloxy of 2-6 carbon atoms, alkynyloxy of 2-6 carbon atoms, hydroxyalkyl of 1-6 carbon atoms, mercaptoalkyl of 1-6 carbon atoms, halomethyl, alkoxymethyl of 2-7 carbon atoms, alkoxy of 1-6 carbon atoms, cycloalkoxy of 3-8 carbon atoms, alkylthio of 1-6 carbon atoms, cycloalkylthio of 3-8 carbon atoms, alkylsulphinyl of 1-6 carbon atoms, alkylsulfonyl of 1-6 carbon atoms, alkylsulfonamido of 1-6 carbon atoms, alkenylsulfonamido of 2-6 carbon atoms, alkynylsulfonamido of 2-6 carbon atoms, cyano, nitro, carboxy, alkoxycarbonyl of 2-7 carbon atoms, alkanoyl of 2-7 carbon atoms, alkenoyl of 3-7 carbon atoms, N-alkyl-N-alkenylamino of 4 to 12 carbon atoms, N,N-dialkenylamino of 6-12 carbon atoms, phenylamino, benzylamino, phenoxy, phenyl, thiophenoxy, benzyl, alkylamino of 1-6 carbon atoms, alkanoyloxy of 2-7 carbon atoms, alkenoyloxy of 3-8 carbon atoms, alkynoyloxy of 3-8 carbon atoms, carbamoyl, N-alkylcarbamoyl of 2-7 carbon atoms, N,N-dialkylcarbamoyl of 3-13 carbon atoms, dialkylamino of 2 to 12 carbon atoms, alkanoyloxymethyl group of 2-7 carbon atoms, alkenoyloxymethyl group of 2-7 carbon atoms, alkynoyloxymethyl group of 2-7 carbon atoms, azido, benzoyl, carboxyalkyl of 2-7 carbons, carboalkoxyalkyl of 3-8 carbon atoms,

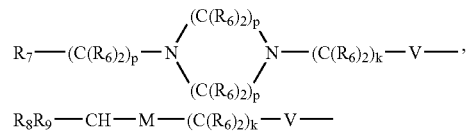

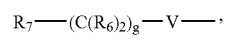

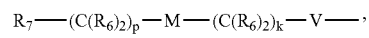

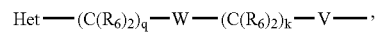

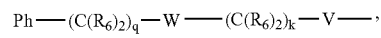

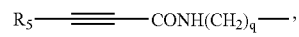

-continued

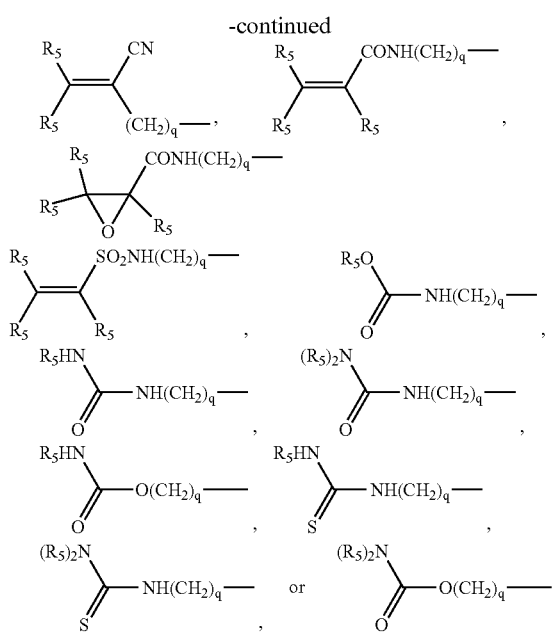

$R_5$ is independently hydrogen, alkyl of 1-6 carbon atoms, aminoalkyl of 1-6 carbon atoms, N-alkylaminoalkyl of 2-9 carbon atoms, N,N-dialkylaminoalkyl of 3-12 carbon atoms, N-cycloalkylaminoalkyl of 4-12 carbon atoms, N-cycloalkyl-N-alkylaminoalkyl of 5-18 carbon atoms, N,N-dicycloalkylaminoalkyl of 7-18 carbon atoms, morpholino-N-alkyl wherein the alkyl group is 1-6 carbon atoms, piperidino-N-alkyl wherein the alkyl group is 1-6 carbon atoms, N-alkyl-piperazino-N-alkyl wherein either alkyl group is 1-6 carbon atoms, azacycloalkyl-N-alkyl of 3-11 carbon atoms, hydroxyalkyl of 1-6 carbon atoms, alkoxyalkyl of 2-8 carbon atoms, phenyl;

V is $(CH_2)_m$, O, S, or $NR_6$;

$R_7$ is $NR_6R_6$, $OR_6$, J, $N(R_6)_3^+$, or $NR_6(OR_6)$;

M is $NR_6$, O, S, $N-[(C(R_6)_2)_pNR_6R_6]$, or $N-[(C(R_6)_2)_p-OR_6]$;

W is $NR_6$, O, S, or is a bond;

Het is a heterocycle selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane pyrrole, and tetrahydropyran; wherein the heterocycle is optionally mono- or di-substituted on carbon or nitrogen with $R_6$; optionally mono- or di-substituted on carbon with hydroxy, $-N(R_6)_2$, or $-OR_6$; optionally mono or di-substituted on carbon with the mono-valent radicals $-(C(R_6)_2)_sOR_6$ or $-[(C(R_6)_2)_sN(R_6)_2]$; or optionally mono or di-substituted on a saturated carbon with divalent radicals $=O$ or $-O(C(R_6)_2)_sO-$;

Ph is a phenyl ring optionally mono-, di- or tri-substituted with halogen, alkyl of 1-6 carbon atoms, trifluoromethyl, nitro, cyano, azido, halomethyl, carboxyl, alkoxycarbonyl, alkylthio, mercapto, mercaptomethyl, $-N(R_6)_2$, $-OR_6$, $(C(R_6)_2)_sOR_6$, $-[(C(R_6)_2)_sN(R_6)_2]$, or $-(C(R_6)_2)_k$Het;

$R_6$ is hydrogen, alkyl of 1-6 carbon atoms, alkenyl of 2-6 carbon atoms, alkynyl of 2-6 carbon atoms, cycloalkyl of 1-6 carbon atoms, alkanoyl of 2-7 carbon atoms, carbamoylalkyl of 2-7 carbon atoms, hydroxyalkyl of 1-6 carbon atoms, hydroxycycloalkyl of 3-6 carbon atoms, or carboxyalkyl of 2-7 carbon atoms; or $R_6$ is phenyl optionally mono-, di-, or tri-substituted with halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, alkoxycarbonyl of 2-7 carbon atoms, phenoxy, phenyl, thiophenoxy, benzoyl, benzyl, phenylamino, benzylamino; alkanoylamino of 1-6 carbon atoms or alkyl of 1-6 carbon atoms;

$R_8$ and $R_9$ are each, independently, $-[(C(R_6)_2)_rNR_6R_6]$, or $-[(C(R_6)_2)_rOR_6]$;

J is independently hydrogen, chlorine, fluorine, or bromine;

g=1-6;

k=0-4;

p=2-4;

q=0-4;

r=1-4;

s=1-6;

m is 0-3;

which process comprises:

(a) reacting a substituted bicyclo[4.2.0]octa-1(6),2,4-triene-7-carbonitrile of formula 1

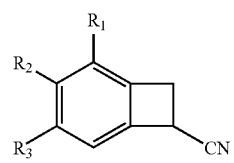

wherein $R_1$, $R_2$, and $R_3$ are defined as above;

with a base to form a first intermediate having the corresponding anion alpha to the cyano group;

(b) reacting said first intermediate with a suitable electrophilic sulfur group to yield an alpha-sulfenylated 1-cyanobenzocyclobutene of formula 2

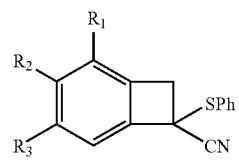

wherein $R_1$, $R_2$, $R_3$, and Ph are defined as above;

(c) reacting an anionic salt of an alkyl or aryl ester or acetonitrile with said cyanobenzocyclobutenes of formula 2 to provide an amino ester or amino nitrile intermediate of formula 3

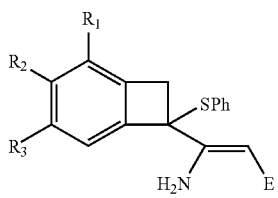

wherein $R_1$, $R_2$, $R_3$, Ph, and E are defined as above; and (d) refluxing the formula 3 adducts in a solvent to provide the substituted esters or nitriles of formula A.

The invention also relates to certain related processes to make substituted benzo[g]quinoline-3-carbonitriles and benzo[g]quinazolines and certain intermediates formed in the aforementioned processes.

DESCRIPTION OF THE INVENTION

The invention provides a novel method for the synthesis of 6,7,8-substituted 3-amino-2-naphthoates or 3-amino-2-naphthonitriles (A), 4,6,7,8-substituted benzo[g]quinoline-3-carbonitriles (B) and 4,6,7,8-substituted benzo[g]quinazolines (C) with complete regiochemical control and in high yields. This constitutes a significant advantage over previously described methods. From the key intermediate A, the compounds B and C can be constructed as single geometric isomers.

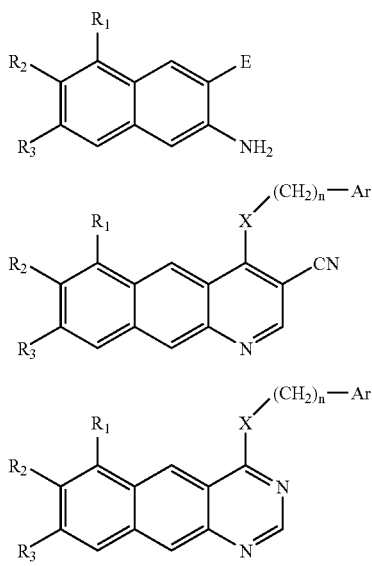

Wherein:

E is cyano or E is an alkoxycarbonyl of 2-12 carbons, —CO$_2$Ph, —CO$_2$-L, cycloalkoxycarbonyl of 4-12 carbons, alkenyloxycarbonyl of 3-12 carbons, cycloalkenyloxycarbonyl of 5-12 carbons, alkynyloxycarbonyl of 4-12 carbons, which may be substituted on a carbon atom with one or more $R_6$ groups;

Ar is cycloalkyl of 3 to 7 carbon atoms, which may be optionally substituted with one or more alkyl of 1 to 6 carbon atoms; or Ar is a pyridinyl, pyrimidinyl, or phenyl ring; wherein the pyridinyl, pyrimidinyl, or phenyl ring may be optionally mono-, di-, or tri-substituted with substituent(s) independently selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, alkoxycarbonyl of 2-7 carbon atoms, alkanoyl of 2-7 carbon atoms, benzoyl, amino, alkylamino of 1-6 carbon atoms, dialkylamino of 2 to 12 carbon atoms, alkanoylamino of 1-6 carbon atoms, alkenoylamino of 3-8 carbon atoms, alkynoylamino of 3-8 carbon atoms, alkanoyloxy of 1-6 carbon atoms, alkenoyloxy of 3-8 carbon atoms, alkynoyloxy of 3-8 carbon atoms, carbamoyl, N-alkylcarbamoyl of 2-7 carbon atoms, N,N-dialkylcarbamoyl of 3-13 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 3-9 carbon atoms, N,N-dialkylaminoalkoxy of 4-10 carbon atoms, mercapto, methylmercapto and benzoylamino; or Ar is a bicyclic aryl or bicyclic heteroaryl ring system of 8 to 12 atoms where the bicyclic heteroaryl ring may contain 1 to 4 heteroatoms selected from N, O, and S wherein the bicyclic aryl or bicyclic heteroaryl ring may be optionally mono- di-, tri, or tetra-substituted with substituent(s) independently selected from the group consisting of halogen, oxo, thiocarbonyl, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, alkoxycarbonyl of 2-7 carbon atoms, alkanoyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 3-9 carbon atoms, N,N-dialkylaminoalkoxy of 4-10 carbon atoms, mercapto, methylmercapto, alkanoyloxy of 1-6 carbon atoms, alkenoyloxy of 3-8 carbon atoms, alkynoyloxy of 3-8 carbon atoms, carbamoyl, N-alkylcarbamoyl of 2-7 carbon atoms, N,N-dialkylcarbamoyl of 3-13 carbon atoms, and benzoylamino; or Ar is the radical:

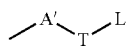

A' is a pyridinyl, pyrimidinyl, or phenyl ring; wherein the pyridinyl, pyrimidinyl, or phenyl ring may be optionally mono- or di-substituted with substituent(s) independently selected from the group consisting of alkyl of 1-6 carbon atoms, alkenyl of 2-6 carbon atoms, alkynyl of 2-6 carbon atoms, azido, hydroxyalkyl of 1-6 carbon atoms, halogen, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, alkoxycarbonyl of 2-7 carbon atoms, alkanoyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 3-9 carbon atoms, N,N-dialkylaminoalkoxy of 4-10 carbon atoms, mercapto, methylmercapto, alkanoyloxy of 1-6 carbon atoms, alkenoyloxy of 3-8 carbon atoms, alkynoyloxy of 3-8 carbon atoms, carbamoyl, N-alkylcarbamoyl of 2-7 carbon atoms, N,N-dialkylcarbamoyl of 3-13 carbon atoms, and benzoylamino;

T is substituted on A' at carbon and is —NH(CH$_2$)$_m$—, —(CH$_2$)$_m$—, —S(CH$_2$)$_m$—, —NR(CH$_2$)$_m$—, —(CH$_2$)$_m$—, —(CH$_2$)$_m$NH—, —(CH$_2$)$_m$O—, —(CH$_2$)$_m$S—, —SO(CH$_2$)$_m$—, —SO$_2$(CH$_2$)$_m$—, —CO(CH$_2$)$_m$—, —(CH$_2$)$_m$CO—, —(CH$_2$)$_m$SO—, —(CH$_2$)$_m$SO$_2$— or —(CH$_2$)$_m$NR—;

L is a phenyl ring that is optionally substituted with one, two, or three substituent(s) independently selected from the group consisting of alkyl of 1-6 carbon atoms, alkenyl of 2-6 carbon atoms, alkynyl of 2-6 carbon atoms, azido, hydroxyalkyl of 1-6 carbon atoms, halogen, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, alkoxycarbonyl of 2-7 carbon atoms, alkanoyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 3-9 carbon atoms, N,N-dialkylaminoalkoxy of 4-10 carbon atoms, mercapto, methylmercapto, alkanoyloxy of 1-6 carbon atoms, alkenoyloxy of 3-8 carbon atoms, alkynoyloxy of 3-8 carbon atoms, carbamoyl, N-alkylcarbamoyl of 2-7 carbon atoms, N,N-dialkylcarbamoyl of 3-13 carbon atoms, and benzoylamino; or L is a 5- or 6-membered heteroaryl ring where the heteroaryl ring contains 1 to 3 heteroatom(s) independently selected from N, O, and S and where the heteroaryl ring may be optionally mono- or di-substituted with substituent(s) independently selected from the group consisting of halogen, oxo, thiocarbonyl, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, alkoxycarbonyl of 2-7 carbon atoms, alkanoyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 3-9 carbon atoms, N,N-dialkylaminoalkoxy of 4-10 carbon atoms, mercapto, methylmercapto, alkanoyloxy of 1-6 carbon atoms, alkenoyloxy of 3-8 carbon atoms, alkynoyloxy of 3-8 carbon atoms, carbamoyl, N-alkylcarbamoyl of 2-7 carbon atoms, N,N-dialkylcarbamoyl of 3-13 carbon atoms, and benzoylamino;

m is 0-3;

n is 0-1;

X is NH, O, S, or NR;

R is alkyl of 1-6 carbon atoms;

$R_1$, $R_2$ and $R_3$ are each, independently, hydrogen, halogen, hydroxy, amino, arylamino, arylalkylamino, hydroxyamino, trifluoromethyl, trifluoromethoxy, mercapto, alkyl of 1-6 carbon atoms, cycloalkyl of 3-8 carbon atoms, alkenyl of 2-6 carbon atoms, alkynyl of 2-6 carbon atoms, alkenyloxy of 2-6 carbon atoms, alkynyloxy of 2-6 carbon atoms, hydroxyalkyl of 1-6 carbon atoms, mercaptoalkyl of 1-6 carbon atoms, halomethyl, alkoxymethyl of 2-7 carbon atoms, alkoxy of 1-6 carbon atoms, cycloalkoxy of 3-8 carbon atoms, alkylthio of 1-6 carbon atoms, cycloalkylthio of 3-8 carbon atoms, alkylsulphinyl of 1-6 carbon atoms, alkylsulfonyl of 1-6 carbon atoms, alkylsulfonamido of 1-6 carbon atoms, alkenylsulfonamido of 2-6 carbon atoms, alkynylsulfonamido of 2-6 carbon atoms, cyano, nitro, carboxy, alkoxycarbonyl of 2-7 carbon atoms, alkanoyl of 2-7 carbon atoms, alkenoyl of 3-7 carbon atoms, N-alkyl-N-alkenylamino of 4 to 12 carbon atoms, N,N-dialkenylamino of 6-12 carbon atoms, phenylamino, benzylamino, phenoxy, phenyl, thiophenoxy, benzyl, alkylamino of 1-6 carbon atoms, alkanoyloxy of 2-7 carbon atoms, alkenoyloxy of 3-8 carbon atoms, alkynoyloxy of 3-8 carbon atoms, carbamoyl, N-alkylcarbamoyl of 2-7 carbon atoms, N,N-dialkylcarbamoyl of 3-13 carbon atoms, dialkylamino of 2 to 12 carbon atoms, alkanoyloxymethyl group of 2-7 carbon atoms, alkenoyloxymethyl group of 2-7 carbon atoms, alkynoyloxymethyl group of 2-7 carbon atoms, azido, benzoyl, carboxyalkyl of 2-7 carbons, carboalkoxyalkyl of 3-8 carbon atoms,

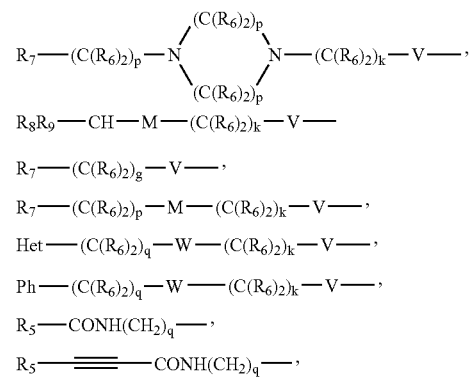

-continued

[chemical structures:
$R_5$, CN, $R_5$, $(CH_2)_q$—;
$R_5$, CONH$(CH_2)_q$—, $R_5$, $R_5$;
$R_5$, CONH$(CH_2)_q$—, O, $R_5$;
$R_5$, SO$_2$NH$(CH_2)_q$—, $R_5$, $R_5$;
$R_5$O, O, NH$(CH_2)_q$—;
$R_5$HN, O, NH$(CH_2)_q$—;
$(R_5)_2$N, O, NH$(CH_2)_q$—;
$R_5$HN, O, O$(CH_2)_q$—;
$R_5$HN, S, NH$(CH_2)_q$—;
$(R_5)_2$N, S, NH$(CH_2)_q$— or;
$(R_5)_2$N, O, O$(CH_2)_q$—;]

$R_5$ is independently hydrogen, alkyl of 1-6 carbon atoms, aminoalkyl of 1-6 carbon atoms, N-alkylaminoalkyl of 2-9 carbon atoms, N,N-dialkylaminoalkyl of 3-12 carbon atoms, N-cycloalkylaminoalkyl of 4-12 carbon atoms, N-cycloalkyl-N-alkylaminoalkyl of 5-18 carbon atoms, N,N-dicycloalkylaminoalkyl of 7-18 carbon atoms, morpholino-N-alkyl wherein the alkyl group is 1-6 carbon atoms, piperidino-N-alkyl wherein the alkyl group is 1-6 carbon atoms, N-alkyl-piperazino-N-alkyl wherein either alkyl group is 1-6 carbon atoms, azacycloalkyl-N-alkyl of 3-11 carbon atoms, hydroxyalkyl of 1-6 carbon atoms, alkoxyalkyl of 2-8 carbon atoms, phenyl;

V is $(CH_2)_m$, O, S, or $NR_6$;

$R_7$ is $NR_6R_6$, $OR_6$, J, $N(R_6)_3^+$, or $NR_6(OR_6)$;

M is $NR_6$, O, S, $N-[(C(R_6)_2)_p NR_6R_6]$, or $N-[(C(R_6)_2)_p-OR_6]$;

W is $NR_6$, O, S, or is a bond;

Het is a heterocycle selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane pyrrole, and tetrahydropyran; wherein the heterocycle is optionally mono- or di-substituted on carbon or nitrogen with $R_6$; optionally mono- or di-substituted on carbon with hydroxy, $-N(R_6)_2$, or $-OR_6$; optionally mono or di-substituted on carbon with the mono-valent radicals $-(C(R_6)_2)_s OR_6$ or $-[(C(R_6)_2)_s N (R_6)_2]$; or optionally mono or di-substituted on a saturated carbon with divalent radicals =O or $-O(C(R_6)_2)_s O-$;

Ph is a phenyl ring optionally mono-, di- or tri-substituted with halogen, alkyl of 1-6 carbon atoms, trifluoromethyl, nitro, cyano, azido, halomethyl, carboxyl, alkoxycarbonyl, alkylthio, mercapto, mercaptomethyl, $-N(R_6)_2$, $-OR_6$, $-(C(R_6)_2)_s OR_6$, $-[(C(R_6)_2)_s N(R_6)_2]$, or $-(C(R_6)_2)_k$Het;

$R_6$ is hydrogen, alkyl of 1-6 carbon atoms, alkenyl of 2-6 carbon atoms, alkynyl of 2-6 carbon atoms, cycloalkyl of 1-6 carbon atoms, alkanoyl of 2-7 carbon atoms, carbamoylalkyl of 2-7 carbon atoms, hydroxyalkyl of 1-6 carbon atoms, hydroxycycloalkyl of 3-6 carbon atoms, or carboxyalkyl of 2-7 carbon atoms; or $R_6$ is phenyl optionally mono-, di-, or tri-substituted with halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, alkoxycarbonyl of 2-7 carbon atoms, phenoxy, phenyl, thiophenoxy, benzoyl, benzyl, phenylamino, benzylamino; alkanoylamino of 1-6 carbon atoms or alkyl of 1-6 carbon atoms;

$R_8$ and $R_9$ are each, independently, $-[(C(R_6)_2)_r NR_6R_6]$, or $-[(C(R_6)_2)_r OR_6]$;

J is independently hydrogen, chlorine, fluorine, or bromine;

g=1-6;
k=0-4;
p=2-4;
q=0-4;
r=1-4;
s=1-6;

or a pharmaceutically acceptable salt thereof;

provided that when $R_5$ is bound to a nitrogen atom, the resulting structures do not include $-N-C-N-$ or $-O-C-N-$ radicals; and when $R_5$ is bound to an oxygen atom, the resulting structures do not include an $-N-C-$ radical;

provided that when $R_6$ is alkenyl of 2-7 carbon atoms or alkynyl of 2-7 carbon atoms, the alkenyl or alkynyl moieties are bound to a nitrogen or oxygen atom through a saturated carbon atom in the alkenyl or alkynyl chain;

provided that when V is $NR_6$ and $R_7$ is $NR_6R_6$, $N(R_6)_3^+$, or $NR_6(OR_6)$, then g=2-6;

provided that when M is O or S and $R_7$ is $OR_6$, then p=1-4;

provided that when V is $NR_6$, O, S, then k=2-4;

provided that when V is O or S and M or W is O or S, then k=1-4 provided that when W is not a bond with Het bonded through a nitrogen atom then q=2-4; and finally provided when W is a bond with Het bonded through a nitrogen atom and V is O or $NR_6$ or S, then k=2-4.

The pharmaceutically acceptable salts are any salts conventionally used in the pharmaceutical industry including those derived from such organic and inorganic acids such as: acetic, lactic, citric, tartaric, succinic, maleic, malonic, gluconic, hydrochloric, hydrobromic, phosphoric, nitric, sulfuric, methanesulfonic, and similarly known acceptable acids.

It is understood by one skilled in the art that the heteroaryl or bicyclic heteroaryl rings of the compounds of Formula I do not contain O—O, S—S, or S—O bonds, as they would be unstable. Preferred bicyclic aryl or bicyclic heteroaryl ring systems include naphthalene, tetralin, indan, 1-indanone, 1,2,3,4-tetrahydroquinoline, naphthyridine, benzofuran, 3-oxo-1,3-dihydroisobenzofuran, benzothiophene, 1,1-dioxo-benzothiophene, indole, indoline 1,3-dioxo-2,3-dihydro-1H-isoindole, benzotriazole, 1H-indazole, indoline, indazole, 1,3-benzodioxole, benzoxazole, purine, phthalimide, coumarin, chromone, quinoline, terahydroquinoline, isoquinoline, benzimidazole, quinazoline, pyrido[2,3-b]pyridine, pyrido[3,4b]pyrazine, pyrido[3,2-c]pyridazine, pyrido[3,4-b]pyridine, 1H-pyrazole[3,4-d]pyrimidine, 1,4-benzodioxane, pteridine, 2(1H)-quinolone, 1(2H)-isoquinolone, 2-oxo-2,3-dihydrobenzthiazole, 1,2-methylene-dioxybenzene, 2-oxindole, 1,4-benzisoxazine, benzothiazole, quinoxaline, quinoline-N-oxide, isoquinoline-N-oxide, quinoxaline-N-oxide, quinazoline-N-oxide, benzoazine, phthalazine, 1,4-dioxo-1,2,3,4-tetrahydrophthalazine, 2-oxo-1,2-dihydroquinoline, 2,4-dioxo-1,4-dihydro-2H-benzo[d][1,3]oxazine, 2,5-dioxo-2,3,4,5-tetrahydro-1H-benzo[e][1,4]diazepine, or cinnoline.

When L is a 5 or 6-membered heteroaryl ring, preferred heteroaryl rings are pyridine, pyrimidine, imidazole, thiazole, thiazolidine, pyrrole, furan, thiophene, oxazole, or 1,2,4-triazole.

Either or both rings of the bicyclic aryl or bicyclic heteroaryl group may be fully unsaturated, partially saturated, or fully saturated. An oxo substituent on the bicyclic aryl or bicyclic heteroaryl moiety means that one of the carbon atoms has a carbonyl group. A thiocarbonyl substituent on the bicyclic aryl or bicyclic heteroaryl moiety means that one of the carbon atoms has a thiocarbonyl group.

When L is a 5 or 6-membered heteroaryl ring, it may be fully unsaturated, partially saturated, or fully saturated. The heteroaryl ring can be bound to A' via carbon or nitrogen. An oxo substituent on the heteroaryl ring means that one of the carbon atoms has a carbonyl group. A thio substituent on the heteroaryl ring means that one of the carbon atoms has a thiocarbonyl group.

The alkyl portion of the alkyl, alkoxy, alkanoyloxy, alkoxymethyl, alkanoyloxymethyl, alkylsulphinyl, alkylsulfonyl, alkylsulfonamido, alkoxycarbonyl, carboxyalkyl, carboalkoxyalkyl, alkanoylamino, N-alkylcarbamoyl, N,N-dialkylcarbamoyl, N-alkylaminoalkoxy and N,N-dialkylaminoalkoxy include both straight chain as well as branched carbon chains. The cycloalkyl portions of cycloalkyl, N-cycloalkylamino, N-cycloalkyl-N-alkylaminoalkyl, N,N-dicycloalkylaminoalkyl, cycloalkylthio and azacycloalkyl substituents include both simple carbocycles as well as carbocycles containing alkyl substituents. The alkenyl portion of the alkenyl, alkenyloxy, alkenylsulfonamido, substituents include both straight chain as well as branched carbon chains and one or more sites of unsaturation and all possible configurational isomers. The alkynyl portion of the alkynyl, alkynylsulfonamido, alkynyloxy, substituents include both straight chain as well as branched carbon chains and one or more sites of unsaturation. Carboxy is defined as a —$CO_2H$ radical. Alkoxycarbonyl of 2-7 carbon atoms is defined as a —$CO_2R''$ radical, where R'' is an alkyl radical of 1-6 carbon atoms. Carboxyalkyl is defined as a $HO_2C$—R'''— radical where R''' is a divalent alkyl radical of 1-6 carbon atoms. Carboalkoxyalkyl is defined as a R''$O_2C$—R'''— radical where R''' is a divalent alkyl radical and where R'' and R''' may be the same or different, and together have 2-7 carbon atoms. Alkanoyl is defined as a —COR'' radical, where R'' is an alkyl radical of 1-6 carbon atoms. Alkenoyl is defined as a —COR'' radical, where R'' is an alkenyl radical of 2-6 carbon atoms. Alkanoyloxy is defined as a —OCOR'' radical, where R'' is an alkyl radical of 1-6 carbon atoms. Alkanoyloxymethyl is defined as R''$CO_2CH_2$— radical, where R'' is an alkyl radical of 1-6 carbon atoms. Alkoxymethyl is defined as R''$OCH_2$— radical, where R'' is an alkyl radical of 1-6 carbon atoms. Alkylsulphinyl is defined as R''SO— radical, where R'' is an alkyl radical of 1-6 carbon atoms. Alkylsulfonyl is defined as R''$SO_2$-radical, where R'' is an alkyl radical of 1-6 carbon atoms. Alkylsulfonamido, alkenylsulfonamido, alkynylsulfonamido are defined as R''$SO_2$NH— radical, where R'' is an alkyl radical of 1-6 carbon atoms, an alkenyl radical of 2-6 carbon atoms, or an alkynyl radical of 2-6 carbon atoms, respectively. N-alkylcarbamoyl is defined as R''NHCO— radical, where R'' is an alkyl radical of 1-6 carbon atoms. N,N-dialkylcarbamoyl is defined as R''R'NCO— radical, where R'' is an alkyl radical of 1-6 carbon atoms, R' is an alkyl radical of 1-6 carbon atoms and R' and R'' may be the same or different.

Het is a heterocycle, as defined above which may be optionally mono- or di-substituted with $R_6$ on carbon or nitrogen, optionally mono- or di-substituted on carbon with hydroxy, —$N(R_6)_2$, or —$OR_6$, optionally mono or di-substituted on carbon with —$(C(R_6)_2)_sOR_6$ or —$(C(R_6)_2)_sN(R_6)_2$, and optionally mono or di-substituted on a saturated carbon with divalent =O or —$O(C(R_6)_2)_sO$— (carbonyl and ketal groups, respectively); in some cases when Het is substituted with =O (carbonyl), the carbonyl group can be hydrated. Het may be bonded to W when q=0 via a carbon atom on the heterocyclic ring, or when Het is a nitrogen containing heterocycle which also contains a saturated carbon-nitrogen bond, such heterocycle may be bonded to carbon, via the nitrogen when W is a bond. When q=0 and Het is a nitrogen containing heterocycle which also contains an unsaturated carbon-nitrogen bond, that nitrogen atom of the heterocycle may be bonded to carbon when W is a bond and the resulting heterocycle will bear a positive charge. When Het is substituted with $R_6$, such substitution may be on a ring carbon, or in the case of a nitrogen containing heterocycle, which also contains a saturated carbon-nitrogen, such nitrogen may be substituted with $R_6$ or in the case of a nitrogen containing heterocycle, which also contains an unsaturated carbon-nitrogen, such nitrogen may be substituted with $R_6$ in with case the heterocycle will bear a positive charge. Preferred heterocycles include pyridine, 2,6-disubstituted morpholine, 2,5-disubstituted thiomorpholine, 2-substituted imidazole, substituted thiazole, N-substituted imidazole, N-subsitituted 1,4-piperazine, N-subsitituted piperidine, and N-substituted pyrrolidine.

The compounds of this invention may contain one or more asymmetric carbons atoms; in such cases, the compounds of this invention include the individual diastereomers, the racemates, and the individual R and S enantiomers thereof. Some of the compound of this invention may contain one or more double bonds; in such cases, the compounds of this invention include each of the possible configurational isomers as well as mixtures of these isomers.

This invention relates to a method for the regioselective synthesis of 4,6,7,8-substituted benzo[g]quinoline-3-carbonitriles and 4,6,7,8-substituted benzo[g]quinazolines as well as intermediates thereof. The benzo[g]quinoline-3-carbonitriles and benzo[g]quinazolines, as well as the pharmaceutically acceptable salts thereof, prepared by the process of this invention inhibit the action of certain growth factor receptor protein kinases (PTK), thereby inhibiting the abnormal growth of certain cell types. Certain 7,8-disubstituted 4-anilinobenzo[g]quinoline-3-carbonitriles and their use as anti-cancer agents are disclosed in U.S. patent application 09/751,274 filed Dec. 29, 2000, which claims priority from U.S. patent application 60/240,905 filed Dec. 29, 1999, the entire disclosure of both being hereby incorporated by reference.

In accordance with this invention a process for the production of 6,7,8-substituted 3-amino-2-naphthoates or 3-amino-2-naphthonitriles (A) in high purity and as single regioisomers is provided by a process which comprises:

(a) Preparation of alpha-substituted 1-cyanobenzocyclobutenes 2 by reacting the anions of the 1-cyanobenzocyclobutenes 1 with an appropriate electrophile, preferably a diphenyl disulfide or a substituted diphenyl disulfide.

(b) Reaction of an anionic salt of an ester or acetonitrile with the above cyanobenzocyclobutenes 2 to provide amino ester or amino nitrile intermediates 3.

(c) Thermal cyclization of the amino ester or amino nitrile intermediates 3 to provide 6,7,8-substituted 3-amino-2-naphthoates or 6,7,8-substituted 3-amino-2-naphthonitriles (A).

Literature methods exist for construction of the starting material benzocyclobutenes 1 in regioisomerically pure form: e.g., Kametani, T. et al *J. Het. Chem*, 11, 179, (1974), Kametani, T.; kondoh, H.; Tsubuki, M.; Honda, T. *J. Chem. Soc Perkin Trans.* 1, 5 (1990), Kametani, T.; Kato, Honda, T. Fukumoto, K. *J. Chem. Soc Perkin* 1, 2001 (1990), Kametani, T.; Kajiwara, M.; Takahashi, T.; Fukumoto, K. *Tetrahedron*, 31, 949 (1975) and Honda, T. Toya, T. *Heterocycles*, 33, 291 (1992), in which $R_1$, $R_2$ and $R_3$ are alkoxy of 1 to 4 carbon atoms, benzyloxy or alkyl of 1 to 6 carbon atoms. The chemistry outlined in scheme 1 represents a novel reaction sequence which provides 6,7,8-substituted 3-amino-2-naphthoates or 6,7,8-substituted 3-amino-2-naphthonitriles (A) as single regioisomers.

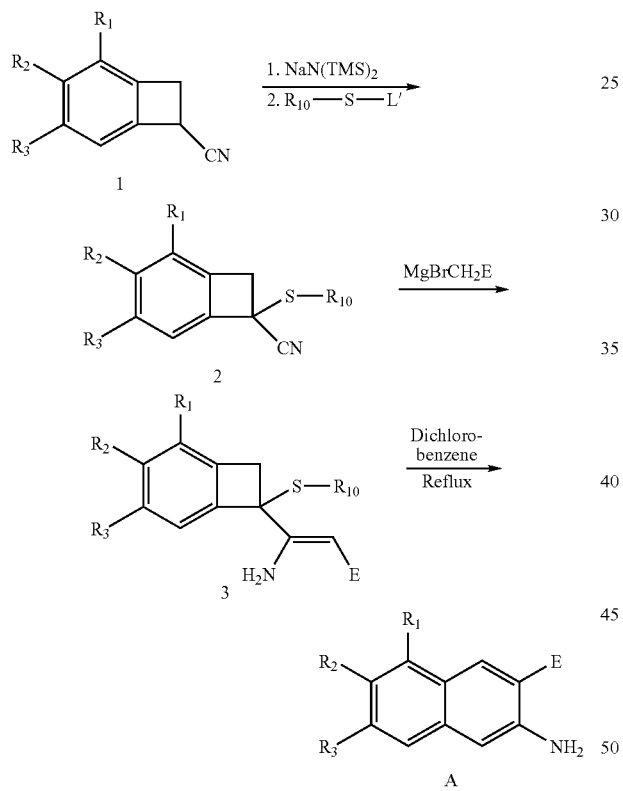

The reaction of the substituted bicyclo[4.2.0]octa-1(6),2,4-triene-7-carbonitriles 1 with a base, preferably a strong base such as sodium (bistrimethylsilyl)amide or n-butyllithium at a temperature of about 0° to about −100° C., preferably about −30° to about −78° C. provides the corresponding anion a to the cyano group which is then reacted with a suitable electrophile $R_{10}$—S-L' where L' is any conventional leaving group, including halogen, alkylthio, phenylthio, benzylthio, heteroarylthio, alkylmethanesulfonate, phenylsulfonate, benzylsulfonate, heteroarylsulfonate, alkylsulfoxide, phenylsulfoxide, benzylsulfoxide, heteroarylsulfoxide, dialkyl amine, or heterocyclic amine such as morpholine, $R_{10}$ is an alkyl of 1-10 carbons, cycloalkyl of 3-10 carbons, alkenyl of 3-10 carbons, cycloalkenyl of 4-10 carbons, alkynyl of 3-10 carbons, Ph or L (where Ph and L are as hereinabove defined), the alkyl, cycloalkyl, alkenyl, cycloalkenyl and alkynyl groups may be optionally substituted with one or more Ph or L groups, a disulfide being preferred and the di-p-chlorophenyl disulfide being especially preferred, and allow the reaction to warm up to about room temperature to provide substituted 7-phenylsulfanylbicyclo[4.2.0]octa-1,3,5-triene-7-carbonitriles 2. Reaction of these intermediates with an acetonitrile or ester anion such as but not limited to zinc exchange from a alkyl bromoacetate or preferably a magnesium bromide salt of acetonitrile or an alkyl ester such as, but not limited to t-butyl acetate in an inert solvent such as ether or tetrahydrofuran and the like provides the corresponding substituted esters or nitriles 3. Refluxing these adducts in a solvent, preferably a solvent with a boiling point in the range of about 140° to about 200° C. such as dichlorobenzene or the like provides the substituted esters or nitriles A. Preferably refluxing the adducts will take less than 5 hours and more preferably from about 0.5 to 3 hours. If $R_{10}$ is Ph or L or $R_{10}$ has an alkyl, cycloalkyl, alkenyl, cycloalkenyl, or alkynyl group substituted with Ph or L, the preferred Ph and L moieties for such $R_{10}$ are a phenyl or heteroaryl group optionally substituted with halogen, alkyl of 1-6 carbons, alkoxy of 1-6 carbons, alkenyl of 2-6 carbon atoms, alkynyl of 2-6 carbon atoms, trifluoromethyl, cyano, or nitro.

Compounds A can be converted to the desired benzo[g] quinoline-3-carbonitriles of Formula B, which possess potent activity as protein kinase inhibitors, by the chemistry shown in scheme 2 and described below.

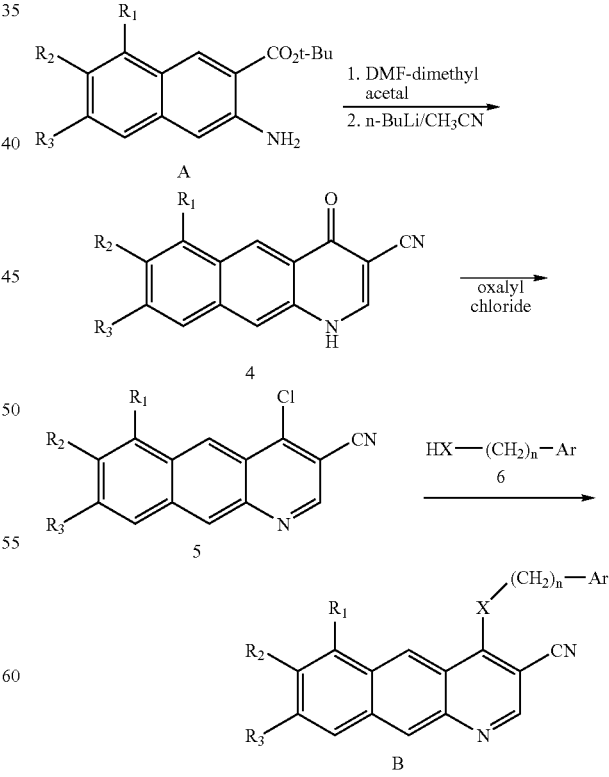

Reaction of 3-amino-2-naphthoic esters (A) with dimethylformamide dialkyl acetal such as dimethylformamide dimethyl acetal, with or without a solvent such as toluene, gives the corresponding amidine intermediates. The reaction of the amidine intermediates with the lithium anion of acetonitrile prepared by using a base such as n-butyllithium or the like in an inert solvent gives 3-cyano-4-oxo-1,4-dihydrobenzo[g]quinolines 4 or the 3-cyano-4-hydroxybenzo[g]quinoline tautomers thereof. Heating 4, with or without solvent, with a halogenating agent preferably a chlorinating agent such as phosphorus oxychloride or oxalyl chloride provides the corresponding 4-chloro-3-cyanobenzo[g]quinolines 5. Condensation of 4-chloro-3-cyanobenzo[g]quinolines 5 with a nucleophilic amine, aniline, mercaptan, thiophenol, phenol, or alcohol reagent of Formula 6, HX—(CH$_2$)$_n$—Ar, wherein Ar, X and n are as hereinbefore defined, give the benzo[g]quinoline-3-carbonitriles of Formula B. The condensation can be carried out at room temperature, but can be accelerated by heating the reaction mixture, preferably to about 800 to 140° C., together with one equivalent of pyridine hydrochloride or by using bases such as trialkylamines, or sodium hydride in an inert solvent, sodium or potassium alkoxides in an alcohol solvent, or by using transition metal catalysts such as tris(dibenzylideneacetone)dipalladium(0) or the like, together with ligands such as, but not limited to 2-dicyclohexylphosphino-2'-(N,N-dimethylamino)biphenyl, and potassium phosphate in an inert solvent.

It will be recognized by those skilled in the art that the 3-cyano-4-hydroxybenzo[g]quinoline tautomer may be converted to leaving groups such as halogen, tosyl, mesyl, aryl- or alkyl-sulfonate, preferably trifluoromethanesulfonate and the like.

When the nucleophile 6 contains primary or secondary amino or hydroxyl groups, it may be necessary to protect these groups prior to the reaction with 4-chloro-3-cyanobenzo[g]quinoline 5. The same amine or alcohol protecting groups described herein below can be used and they can be removed from the products of Formula B as described.

In addition, intermediates A can be converted to benzo[g]quinazolines C. The methodology outlined in Scheme 3 provides for the regioselective synthesis of substituted benzo[g]quinazolines with substituents analogous to those utilized in the case of the benzo[g]quinoline-3-carbonitriles

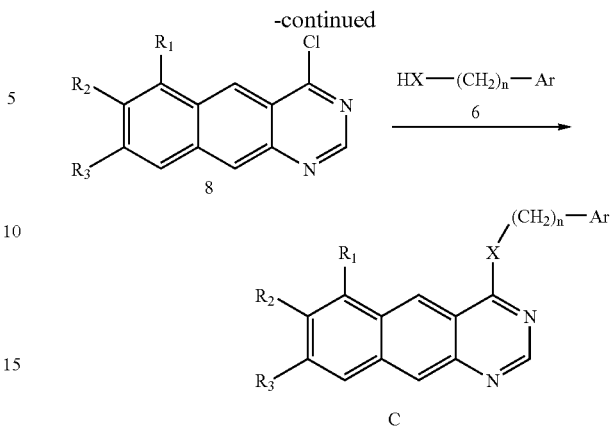

Intermediates A can be converted to compounds 7 by refluxing in formamide or the like for about 1-5 hours. Heating 7, with or without solvent such as toluene, with a halogenating agent, preferably a chlorinating agent such as phosphorus oxychloride or oxalyl chloride, with or without a base such as diethylaniline, provides the corresponding 4-chlorobenzo[g]quinazolines 8. Condensation of 4-chlorobenzo[g]quinazolines 8 with a nucleophilic amine, aniline, mercaptan, thiophenol, phenol, or alcohol reagent of Formula 6, HX—(CH$_2$)$_n$—Ar, wherein Ar, X and n are as hereinbefore defined, give the benzo[g]quinazolines of Formula C. The condensation can be carried out at room temperature or can be accelerated by: heating the reaction mixture together with one equivalent of pyridine hydrochloride; or by using bases such as trialkylamines, sodium hydride in an inert solvent, sodium or potassium alkoxides in an alcohol solvent; or by using transition metal catalysts such as tris(dibenzylideneacetone)dipalladium(0) or the like, together with ligands such as, but not limited to 2-dicyclohexylphosphino-2'-(N,N-dimethylamino)biphenyl, and potassium phosphate or the like in an inert solvent.

When the nucleophile 6 contains primary or secondary amino or hydroxyl groups, it may be necessary to protect these groups prior to the reaction with 4-chloroquinazoline 8. The same amine or alcohol protecting groups described herein below can be used and they can be removed from the products of Formula C as described.

An alternative method to provide 4-anilino-benzo[g]quinazolines is shown in scheme 4.

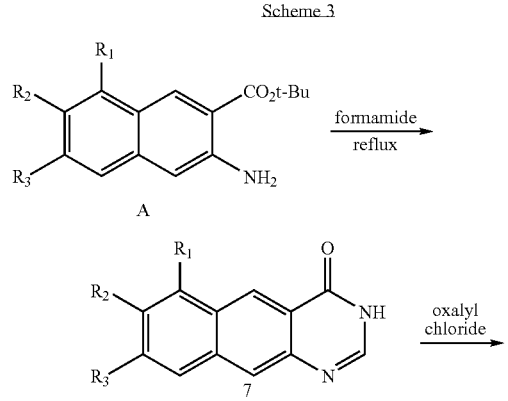

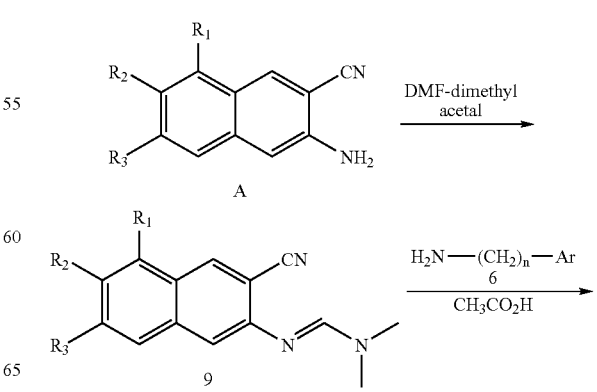

-continued

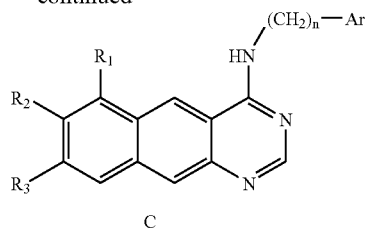

C

Reaction of intermediates A with, for example, dimethylformamide dimethyl acetal, with or without a solvent, gives the corresponding amidine intermediates 9. Heating the amidine intermediates 9 with an appropriately substituted amine 6 in acetic acid, preferably from 50° to 115° C. from 0.5 to 24 hours, provides the products of Formula C.

Converting the $R_1$, $R_2$ and $R_3$ groups to those hereinabove described can be accomplished through any conventionally known techniques, for example:

Where one or more of $R_1$, $R_2$, and $R_3$ of 1, 2, 3, 4, 6, 7, 8, 9 or Formula A, B, or C is a methoxy group, it can be converted to the corresponding hydroxy group by reaction with a demethylating agent such as boron tribromide in an inert solvent or by heating with pyridinium chloride with or without solvent;

where one or more of $R_1$, $R_2$, and $R_3$ of 1, 2, 3, 4, 5, 7, 8, 9 or Formula A, B, or C is a benzyloxy group, it can be converted to the corresponding hydroxy group by reaction with a debenzylating agent such as boron tribromide in an inert solvent, hydrochloric acid, trifluoroacetic acid or catalytic hydrogenation with a catalyst such as palladium-on-carbon;

where one or more of $R_1$, $R_2$, and $R_3$ of 1, 2, 3, 4, 5, 7, 8, 9 or Formula A, B, or C is a hydroxy group, it can be converted to a substituted alkoxy by reacting with an appropriately substituted alcohol using triphenyl phosphine and diethyl azodicarboxylate in an inert solvent, or alternatively by first reacting with a reagent such as, but not limited to, a bromoalkyl chloride or chloroalkyl tosylate to provide an Intermediate which can be converted to the above described groups by subsequent reaction with an appropriately substituted nucleophile.

where one or more of $R_1$, $R_2$, and $R_3$ of 1, 2, 3, 4, 5, 7, 8, 9 or Formula A, B, or C is a hydroxy group, it can be converted to a substituted benzyloxy, substituted phenoxy or cycloalkoxy by reacting with an appropriately substituted alcohol using triphenyl phosphine and diethyl azodicarboxylate in an inert solvent.

where one or more of $R_1$, $R_2$, and $R_3$ of 1, 2, 3, 4, 5, 7, 8, 9 or Formula A, B, or C is a hydroxy group, it can be converted to a trifluoromethanesulfonate using trifluoromethanesulfonate anhydride or N-phenyltrifluoromethylsulfonamide and a base such as triethylamine in an inert solvent;

where one or more of $R_1$, $R_2$, and $R_3$ of 1, 2, 3, 4, 5, 7, 8, 9 or Formula A, B, or C is a trifluoromethanesulfonate, it can be converted to an alkylamino of 1-6 carbons, dialkylamino of 2-12 carbons, benzylamino, dibenzylamino, arylamino, arylalkylamino group by reaction with an appropriately substituted amine and a palladium catalyst such as, but not limited to bis(dibenzylideneacetone)palladium, dichlorobis (tri-ortho tolylphosphine) palladium and ligands such as 2,2'-bis(diphenylphosphinyl)-1,1'-binaphthalene (BINAP), tri-t-butyl phosphine or 1,1'-bis(di-tert-butylphosphino)ferrocene together with or without a base such as sodium t-butoxide in an inert solvent;

where one or more of $R_1$, $R_2$, and $R_3$ of 1, 2, 3, 4, 5, 7, 8, 9 or Formula A, B, or C is a benzylamino or dibenzylamino group, it can be converted to an amino group by catalytic hydrogenation with a catalyst such as palladium-on-carbon, or sodium in ammonia.

In those cases where one or more of $R_1$, $R_2$, and $R_3$ of 1, 2, 3, 4, 5, 7, 8, 9 or Formula A, B, or C may contain an asymmetric carbon atom, the intermediates can be used as the racemate or as the individual R or S enantiomers in which case the compounds of this invention will be in the racemic or R and S optically active forms, respectively. In cases where the substituents may contain more than one asymmetric carbon atom, diastereomers may be present; these can be separated by methods well known in the art including, but not limited to, fractional crystallization and chromatographic methods. When 1, 2, 3, 4, 6, 6, 7, 8, 9 or Formula A, B, or C contains primary or secondary amino groups, it may be necessary to protect these groups prior to the next reaction. Suitable protecting groups include, but are not limited to tert-butoxycarbonyl (BOC), beta-trimethylsilylethanesulfonamide (SES), benzyloxycarbonyl (CBZ) and benzyl (Bn) protecting groups. The first protecting group listed above can be removed from the final products by treatment with an acid such as trifluoroactic acid, the second protecting group with a fluoride salt, such as cesium fluoride or tetrabutylammonium fluoride. The latter two protecting groups can be removed by catalytic hydrogenation or sodium in ammonia. In those cases where 1, 2, 3, 4, 5, 6, 7, 8, 9 or Formula A, B, or C contains hydroxyl groups, the hydroxyl groups may first have to be protected prior to the subsequent reaction. Suitable protecting groups include, but are not limited to, t-butyidimethylsilyl, tetrahydropyranyl, or benzyl protecting groups. The first two protecting groups listed above can be removed from the final products by treatment with an acid such as acetic acid or hydrochloric acid while the latter protecting group can be removed by catalytic hydrogenation.

EXAMPLE 1

5-(Benzyloxy)-1-bromo-2-(bromomethyl)-4-methoxybenzene

4-Benzyloxy-3-methoxybenzyl alcohol (1 g, 4.1 mmol) is dissolved in acetic acid (3 ml) and cooled to 10° C. in a water/ice bath. A solution of bromine (0.25 ml, 4.92 mmol) in acetic acid (0.25 ml) is added dropwise to the reaction mixture while stirring. The reaction is allowed to warm to room temperature and is stirred for 18 hours. The reaction is diluted with water and the resulting precipitate is collected by filtration. The precipitate is washed well with water and recrystallized from a small amount of methanol to yield 1.3 g of 5-(benzyloxy)-1-bromo-2-(bromomethyl)-4-methoxybenzene as a white solid, mp 103-105° C.

$^1$HNMR ($d^6$-DMSO): δ 7.5 (m, 7H); 5.09 (s, 2H); 4.69 (s, 2H); 3.77 (s, 3H)

MS (ES, positive ion mode): m/z calcd for $C_{15}H_{14}Br_2O_2$: 386.08, found (M+H)$^+$ 387.1

Analysis for $C_{15}H_{14}Br_2O_2 \cdot 0.3CH_3OH$ Calcd: C, 47.60; H, 3.84. Found: C, 47.44; H, 3.77.

EXAMPLE 2

3-(4-Benzyloxy-2-bromo-5-methoxyphenyl)-propionitrile

To a solution of n-butyllithium (1.8 mL of a 2.5 M solution in hexane, 4.5 mmol) in 5 mL of tetrahydrofuran is added a solution of acetonitrile (1.0 mL, 19.1 mmol) in 5 mL of tetrahydrofuran. The reaction mixture is stirred at −78° C. for 15 min. A solution of 5-(benzyloxy)-1-bromo-2-(bromomethyl)-4-methoxybenzene (0.7 g, 1.8 mmol) in 3 mL of tetrahydrofuran is added and stirring is continued for 1 hour at −78° C. The reaction is quenched by the addition of 15 mL of water and the mixture is allowed to warm to room temperature. The mixture is extracted with ethyl acetate and the organic layers combined, then dried with sodium sulfate. After reducing in vacuo, the crude product is purified by flash chromatography using a gradient of 95:5 to 4:1 hexanes/ethyl acetate as an eluent. The clean fractions are combined, reduced in vacuo and dried to yield 0.343 g of 3-(4-benzyloxy-2-bromo-5-methoxyphenyl)-propionitrile as a white solid, mp 52-53° C.

$^1$HNMR (d$^6$-DMSO): δ 7.39 (m, 5H); 7.33 (s, 1H); 7.08 (s, 1H); 5.09 (s, 2H); 3.77 (s, 3H); 2.92 (t, 2H; J=5.49), 2.78 (t, 2H; J=5.07).

MS (ES, positive ion mode): m/z calcd for $C_{17}H_{18}BrNO_2$: 346.22, found (M+H)$^+$ 347.1

Analysis for $C_{17}H_{16}BrNO_2$ Calcd: C, 58.98; H, 4.66; N, 4.05. Found: C, 58.77; H, 4.71; N, 3.89.

EXAMPLE 3

4-Benzyloxy-3-methoxybicyclo[4.2.0]octa-1,3,5-triene-7-carbonitrile

A suspension of sodium amide is prepared from 100 mL of liquid ammonia, sodium (0.52 g, 22.8 mmol) and a catalytic amount of ferric nitrate. To this is added 3-(4-benzyloxy-2-bromo-5-methoxyphenyl)-propionitrile (2 g, 5.7 mmol) in portions and the reaction is stirred at −33° C. for 45 minutes. The reaction is then cooled down to −78° C. and quenched with ammonium chloride. The liquid ammonia is allowed to evaporate and the resulting solid residue is washed with water. The tan solid obtained is purified by flash chromatography, using 4:1 hexanes/ethyl acetate as an eluent. The clean fractions are combined and reduced in vacuo to yield 1 g of 4-benzyloxy-3-methoxybicyclo[4.2.0]octa-1,3,5-triene-7-carbonitrile as a clear oil that solidifies into a white solid upon standing, mp 85° C.

$^1$HNMR (d$^6$-DMSO): δ 7.39 (m, 5H); 7.04 (s, 1H); 6.89 (s, 1H); 5.08 (d, 1H, J=12.15); 5.05 (d. 1H, J=12.12); 4.45 (dd, 1H, J=1.74, 3.93), 3.74 (s, 3H); 3.6 (dd, 1H, J=3.99, 10.29), 3.35 (d, 1H, J=1.77)

MS (ES, positive ion mode): m/z calcd for $C_{17}H_{15}NO_2$: 265.31, found (M+H)$^+$ 266.1

Analysis for $C_{17}H_{15}NO_2$ Calcd: C, 76.96; H, 5.70; N, 5.28. Found: C, 76.87; H, 5.97; N, 5.01.

EXAMPLE 4

4-Benzyloxy-7-(4-chloro-phenylsulfanyl)-3-methoxybicyclo[4.2.0]Octa-1,3,5-triene-7-carbonitrile To a solution of 4-benzyloxy-3-methoxybicyclo[4.2.0] octa-1,3,5-triene-7-carbonitrile (1.0 g, 3.7 mmol) in anhydrous tetrahydrofuran (10 mL) at −78° C. is added sodium bis(trimethylsilyl) amide (5.65 mL of a 1M solution in tetrahydrofuran, 5.6 mmol) over a period of 4 minutes, followed by the addition of 4,4'-dichlorodiphenyl disulfide in one portion. The reaction is stirred at −78° C. for 15 minutes and then at room temperature for one hour. The reaction is then diluted and extracted with ethyl acetate. The organic layer is collected and dried with sodium sulfate. After reducing in vacuo, the crude material is purified by flash chromatography using 4:1 hexanes/ethyl acetate. The clean fractions are combined, reduced and dried to yield 1.3 g of 4-benzyloxy-7-(4-chloro-phenylsulfanyl)-3-methoxybicyclo[4.2.0]octa-1,3,5-triene-7-carbonitrile as an off-white solid, mp 114-115° C.

$^1$HNMR (d$^6$-DMSO): δ 7.62-7.54 (m, 4H); 7.41 (m, 4H); 7.36 (m, 1H); 6.97 (s, 1H); 6.83 (s, 1H); 5.08 (dd, 2H, J=9.07, 10.53); 3.98 (d, 1H, J=10.47), 3.78 (s, 3H); 3.60 (d, 1H, J=10.5)

MS (ES, positive ion mode): m/z calcd for $C_{23}H_{18}ClNO_2S$: 408.92, found (M+H)$^+$ 408.1

Analysis for $C_{23}H_{18}ClNO_2S$ Calcd: C, 67.72; H, 4.45; N, 3.43. Found: C, 67.99; H, 4.63; N, 3.33.

EXAMPLE 5

4-Benzyloxy-3-methoxy-7-phenylsulfanylbicyclo [4.2.0]octa-1,3,5-triene-7-carbonitrile To a solution of 4-benzyloxy-3-methoxybicyclo[4.2.0] octa-1,3,5-triene-7-carbonitrile (7.22 g, 3.7 mmol) in anhydrous tetrahydrofuran (60 mL) at −78° C. is added sodium bis(trimethylsilyl)amide (41.0 mL of a 1M solution in tetrahydrofuran, 41.0 mmol) over a period of 4 minutes, followed by the addition of 11.9 g (54.5 mmol) of phenyl disulfide in one portion. The reaction is stirred at −78° C. for 15 minutes and then at room temperature for one hour. The reaction is quenched with water and extracted with ethyl acetate. The organic layers are combined and dried with sodium sulfate. After reducing in vacuo, the crude material is purified by flash chromatography using 4:1 hexanes/ethyl acetate. The clean fractions are combined, reduced and dried to yield 7.0 g of 4-benzyloxy-3-methoxy-7-phenylsulfanyl-bicyclo[4.2.0]octa-1,3,5-triene-7-carbonitrile as a white solid, mp 109-110° C.

$^1$HNMR (d$^6$-DMSO): δ 7.60-7.52 (m, 2H); 7.51-7.48 (m, 3H); 7.42-7.34 (m, 5H); 6.97 (s, 1H); 6.80 (s, 1H); 5.03 (dd, 2H, J=9.0 Hz, 11.4 Hz); 4.01 (d, 1H, J=10.5 Hz); 3.78 (s, 3H); 3.60 (d, 1H, J=10.5)

MS (ES, positive ion mode): m/z calcd for $C_{23}H_{19}NO_2S$: 373.5, found (M+H)$^+$ 374.0

Analysis for $C_{23}H_{19}NO_2S$ Calcd: C, 73.97; H, 5.13; N, 3.75. Found: C, 73.83; H, 5.16; N, 3.53.

EXAMPLE 6

3-Amino-3-[4-benzyloxy-7-(4-chloro-phenylsulfanyl)-3-methoxybicyclo[4.2]octa-1,3,5-trien-7-yl]-acrylic acid tert-butyl ester To a stirred solution of ethylmagnesium bromide (3.26 mL of a 3M solution in diethyl ether, 9.8 mmol) in anhydrous tetrahydrofuran (10 mL) at 0° C. under nitrogen is added diisopropylamine (2.75 mL, 19.6 mmol). The mixture is stirred at 0° C. for 1 hour. t-Butyl acetate (0.5 mL, 3.6 mmol) and a solution of 1.0 g (2.45 mmol) of 4-benzyloxy-7-(4-chloro-phenylsulfanyl)-3-methoxybicyclo[4.2.0]octa-1,3,5-triene-7-carbonitrile in anhydrous tetrahydrofuran (10 mL) are added successively, and the resulting mixture is stirred for an additional hour. The reaction is quenched with aqueous ammonium chloride and the product mixture is extracted with ethyl acetate. The ethyl acetate extract is washed with brine, dried over anhydrous sodium sulfate and passed through a plug of silica to give 3-amino-3-[4-benzyloxy-7-(4-chloro-phenylsulfanyl)-3-methoxybicyclo [4.2.0]octa-1,3,5-trien-7-yl]-acrylic acid tert-butyl ester as a clear oil, that solidifies upon standing, mp 112-115° C.

$^1$HNMR (d$^6$-DMSO): δ 7.60-7.29 (m, 9H); 6.81 (s, 1H); 6.72 (s, 1H); 5.08 (dd, 2H, J=9.09, 11.82 Hz); 4.15 (s, 1H); 3.73 (s, 3H); 3.48 (d, 1H, J=10.7 Hz); 3.30 (d, 1H, J=10.6 Hz); 1.36 (s, 9H)

MS (ES, positive ion mode): m/z calcd for $C_{28}H_{30}ClNO_4S$: 524.1, found (M+H)$^+$ 523.9

Analysis for $C_{29}H_{30}ClNO_4S$ Calcd: C, 66.46; H, 5.77; N, 2.67. Found: C, 66.31; H, 5.91; N, 2.61.

EXAMPLE 7

3-Amino-6-benzyloxy-7-methoxynaphthalene-2-carboxylic acid tert-butyl ester

Nitrogen gas is bubbled through a solution of 3-amino-3-[4-benzyloxy-7-(4-chloro-phenylsulfanyl)-3-methoxybicyclo[4.2.0]octa-1,3,5-trien-7-yl]-acrylic acid tert-butyl ester (0.6 g, 1.1 mmol) in 1,2-dichlorobenzene (100 mL) for 1 hour and the reaction is heated to 179° C. After one hour the reaction is cooled and reduced in vacuo. The residue is washed with ether, dissolved in methylene chloride and purified through a plug of silica eluting with methylene chloride. The filtrate is reduced and dried to afford 0.321 g of 3-amino-6-benzyloxy-7-methoxynaphthalene-2-carboxylic acid tert-butyl ester as a yellow solid, mp 179-180° C.

$^1$HNMR (d$^6$-DMSO): δ 8.18 (s, 1H); 7.4 (m, 5H); 7.18 (s, 1H); 7.01 (s, 1H); 6.85 (s, 1H); 6.21 (s, 2H), 5.17 (s, 2H); 3.74 (s, 3H), 1.58 (s, 9H)

MS (ES, positive ion mode): m/z calcd for $C_{23}H_{25}NO_4$: 379.45, found (M+H)$^+$ 379.9

Analysis for $C_{23}H_{25}NO_4$.0.7 H$_2$O Calcd: C, 70.50; H, 6.08; N, 3.57. Found: C, 70.45; H, 6.24; N, 3.40.

EXAMPLE 8

8-Benzyloxy-7-methoxy-4-oxo-1,4-dihydrobenzo[g] quinoline-3-carbonitrile

In a round bottom flask containing 10 mL of toluene is added 3-amino-6-benzyloxy-7-methoxynaphthalene-2-carboxylic acid tert-butyl ester (3.0 g, 7.9 mmol) and dimethylformamide dimethyl acetal (5.4 mL, 31.6 mmol) under a positive nitrogen flow. The mixture is stirred at 120° C. for 1.5 hour, then is cooled to room temperature. The volatiles are removed under reduced pressure and the resulting residue is dried in vacuo for 15 h to yield 3.0 g of 6-benzyloxy-3-(dimethylamino-methyleneamino)-7-methoxy-naphthalene-2-carboxylic acid tert-butyl ester as a dark oil.

To a solution of n-butyllithium (7.68 mL of a 2.5 M solution in hexane, 19.2 mmol) in 30 mL of tetrahydrofuran is added a solution of acetonitrile (3.34 mL, 64.0 mmol) in 50 mL of tetrahydrofuran. The reaction mixture is stirred at −78° C. for 15 min. A solution of 6-benzyloxy-3-(dimethylamino-methyleneamino)-7-methoxy-naphthalene-2-carboxylic acid tert-butyl ester obtained in the previous step (2.8 g, 6.4 mmol) in 30 mL of tetrahydrofuran is added and stirring is continued for 1 h at −78° C. The reaction is quenched by the addition of 10 mL of glacial acetic acid and the mixture is allowed to warm up to room temperature. The volatiles are removed under reduced pressure and the resulting residue is washed with water, then ethyl acetate and is dried in a vacuum oven to yield 1.9 g of 8-benzyloxy-7-methoxy-4-oxo-1,4-dihydrobenzo[g]quinoline-3-carbonitrile as a yellow solid, mp>300° C.

$^1$HNMR (d$^6$-DMSO+TFA): δ 8.71 (s, 1H); 8.63 (s, 1H); 7.93 (s, 1H); 7.61 (s, 1H); 7.58 (s, 1H); 7.43 (m, 5H); 5.27 (s, 2H), 3.74 (s, 3H)

MS (ES, positive ion mode): m/z calcd for $C_{22}H_{15}N_2O_2$: 356.38, found (M+H)$^+$ 357.1

Analysis for $C_{22}H_{15}N_2O_2$.0.2 H$_2$O Calcd: C, 73.45; H, 4.54; N, 7.77. Found: C, 73.49; H, 4.49; N, 7.65.

EXAMPLE 9

3-Amino-6-hydroxy-7-methoxy-naphthalene-2-carboxylic acid tert-butyl ester

A solution of 4.7 g (12.0 mmol) of 3-amino-6-benzyloxy-7-methoxynaphthalene-2-carboxylic acid tert-butyl ester and 2.0 g of 10% Pd/C in 40 mL of DMF and 100 mL of methanol is shaken on Parr shaker at 40 psi for 18 hours. The hydrogenation is repeated twice more to bring the reaction to completion. The catalyst is filtered through a pad of Celite, is washed with methanol and solvent is evaporated to yield a residue which is dissolved in methylene chloride. This is then filtered through a short pad of Magnesol and is washed with methylene chloride and ethyl acetate. The filtrate is evaporated to yield 3.4 g of 3-amino-6-hydroxy-7-methoxy-naphthalene-2-carboxylic acid tert-butyl ester as a yellow solid, mp 262-263° C.

$^1$HNMR (d$^6$-DMSO): δ 9.61 (bs, 1H); 8.15 (s, 1H); 7.13 (s, 1H); 6.74 (d, 2H, J=2.7); 6.12 (s, 2H); 3.82 (s, 3H), 1.58 (s, 9H)

MS (ES, positive ion mode): m/z calcd for $C_{16}H_{19}NO_4$: 289.33, found (M+H)$^+$ 289.9

Analysis for $C_{16}H_{19}NO_4$.0.1CH$_3$CO$_2$C$_2$H$_5$ Calcd: C, 66.06; H, 6.69; N, 4.70. Found: C, 66.30; H, 6.96; N, 4.30.

EXAMPLE 10

3-Amino-7-methoxy-6-(2-morpholinyl-4-yl-ethoxy)-naphthalene-2-carboxylic acid tert-butyl ester To a solution of 0.72 g (2.49 mmol) of 3-amino-6-hydroxy-7-methoxy-naphthalene-2-carboxylic acid tert-butyl ester in 7.5 ml of tetrahydrofuran is added 0.46 mL (3.74 mmol) of 4-(2-hydroxyethyl)morpholine, followed by the addition of 1.34 g (4.98 mmol) of diphenyl-2-pyridylphosphine and 0.6 mL (3.87 mmol) of diethyl azadicarboxylate. The resulting mixture is stirred at room temperature for 1.5 hours, quenched with water, diluted with ethyl acetate and the two layers are separated. The organic layer is extracted with 0.2N hydrochloric acid. After neutralizing the aqueous layer with a saturated solution of sodium bicarbonate, it is extracted with ethyl acetate. The ethyl acetate extract is dried over anhydrous sodium sulfate, filtered and evaporated to yield a brown oil. The oil is purified by silica gel chromatography, utilizing a gradient of ethyl acetate/hexane (85:15 to 100:0), to give 0.7 g of 3-amino-7-methoxy-6-(2-morpholin-4-yl-ethoxy)-naphthalene-2-carboxylic acid tert-butyl ester as an orange solid, mp 125-127° C.

$^1$HNMR (CDCl$_3$): δ 8.24 (s, 1H); 7.00 (s, 1H); 6.81 (d, 2H, J=2.34 Hz); 5.47 (bs, 2H); 4.26 (t, 2H, J=4.5 Hz); 3.92 (s, 3H); 3.75 (t, 4H, J=3.45 Hz); 2.93 (t, 2H, J=4.5 Hz); 2.65 (bs, 4H); 1.63 (s, 9H).

MS (ES, positive ion mode): m/z calcd for $C_{22}H_{30}N_2O_5$: 402.4, found (M+H)$^+$ 403.3

Analysis for $C_{22}H_{30}N_2O_5$ Calcd: C, 65.65; H, 7.51; N, 6.96. Found: C, 65.65; H, 7.30; N, 6.98.

EXAMPLE 11

7-Methoxy-8-(2-morpholin-4-yl-ethoxy)-3H-benzo [g]quinazolin-4-one

A mixture of 3.5 g (8.6 mmol) of 3-amino-7-methoxy-6-(2-morpholin-4-yl-ethoxy)-naphthalene-2-carboxylic acid tert-butyl ester and 60 ml of formamide is heated at 178° C. for 2 hours, then cooled. To this is added 4:1 methylene chloride/methanol. The resulting solution is washed several times with brine, dried over anhydrous sodium sulfate and evaporated to yield an oil. The oil is purified by silica gel chromatography, utilizing a gradient of 99:1 to 88:12 methylene chloride/methanol to give sticky solid, which is triturated with ethyl acetate to yield 1.5 g of 7-methoxy-8-(2-morpholin-4-yl-ethoxy)-3H-benzo[g]quinazolin-4-one as a tan solid, mp 230-232° C.

$^1$HNMR ($d^6$-DMSO+trifluoroacetic acid): δ 9.39 (s, 1H); 8.83 (s, 1H); 8.17 (s, 1H); 7.80 (s, 1H); 7.77 (s, 1H); 4.63 (t, 2H, J=3.3 Hz,); 4.05 (d, 2H, J=8.9 Hz); 3.99 (s, 3H); 3.76 (m, 4H); 3.66 (d, 2H, J=9.3 Hz); 3.34 (m, 2H).

MS (ES, positive ion mode): m/z calcd for $C_{19}H_{21}N_3O_4$: 355.4, found (M+H)$^+$ 355.9

Analysis for $C_{19}H_{21}N_3O_4$·0.2 $CH_3CO_2C_2H_5$ Calcd: C, 63.75; H, 6.11; N, 11.27. Found: C, 64.13; H, 6.04; N, 10.93.

EXAMPLE 12

7-Methoxy-8-(2-morpholin-4-yl-ethoxy)-4-oxo-1,4-dihydrobenzo[g]quinoline-3-carbonitrile A mixture of 0.69 g (1.7 mmol) of 3-amino-7-methoxy-6-(2-morpholin-4-yl-ethoxy)-naphthalene-2-carboxylic acid tert-butyl ester and 2.4 mL of N,N-dimethylformamide dimethyl acetal in 7.0 mL of toluene is heated under reflux for 1.5 hours. The solvent is evaporated and the residue is dried on high vacuum to yield 3-(dimethylamino-methyleneamino)-7-methoxy-6-(2-morpholin-4-yl-ethoxy)naphthalene-2-carboxylic acid tert-butyl ester as purple white foam.

To 15 mL of tetrahydrofuran at −78° C. is added 2.6 mL of n-butyllithium (1.6M in hexane) and the reaction mixture is stirred for 5 minutes. To this is added 0.36 mL (6.8 mmol) of acetonitrile dropwise, followed by stirring for 15 minutes. Finally, a solution of 3-(dimethylamino-methyleneamino)-7-methoxy-6-(2-morpholin-4-yl-ethoxy)naphthalene-2-carboxylic acid tert-butyl ester in 5 mL of tetrahydrofuran is added dropwise over a period of 15 minutes. The resulting mixture is stirred at −78° C. for 1 hour, then at room temperature for 1 hour. After cooling again to −78° C., the reaction is quenched with 0.5 mL of glacial acetic acid, the dry ice bath is removed and the resulting thick slurry is stirred for 1 hour. The solid is collected by filtration, washed with ethyl acetate and dried. Purification is carried out by silica gel chromatography, utilizing a gradient of 95:5 to 89:11 of methylene chloride/methanol to give 0.38 g of 7-methoxy-8-(2-morpholin-4-yl-ethoxy)-4-oxo-1,4-dihydrobenzo[g]quinoline-3-carbonitrile as a yellow solid, mp 275° C. (dec).

$^1$HNMR ($d^6$-DMSO+trifluoroacetic acid): δ 8.74 (s, 1H); 8.69 (s, 1H); 8.00 (s, 1H); 7.65 (s, 1H); 7.59 (s, 1H); 4.59 (t, 2H, J=3.3 Hz,); 4.05 (d, 2H, J=9.2 Hz); 3.97 (s, 3H); 3.75 (m, 4H); 3.66 (d, 2H, J=9.3 Hz); 3.34 (t, 2H, J=7.0 Hz).

MS (ES, positive ion mode): m/z calcd for $C_{21}H_{21}N_3O_4$: 379.4, found (M+H)$^+$ 380.2

Analysis for $C_{21}H_{21}N_3O_4$·2.5H$_2$O Calcd: C, 60.71; H, 6.07; N, 10.12. Found: C, 60.93; H, 6.11; N, 9.76.

EXAMPLE 13

8-Hydroxy-7-methoxy-4-oxo-1,4-dihydrobenzo[g] quinoline-3-carbonitrile

A solution of 3.6 g (7.3 mmol) of 8-benzyloxy-7-methoxy-4-oxo-1,4-dihydrobenzo[g]quinoline-3-carbonitrile and 0.7 g of 10% Pd/C in 240 mL of dimethyl formamide is hydrogenated in a Parr shaker at 40 psi for 24 hours. The catalyst is filtered through a pad of Celite, Is washed with dimethyl formamide and the solvent is reduced in vacuo to yield a solid. The crude product is suspended in ether, collected by filtration, further washed with ether and dried to yield 3.0 g of 8-hydroxy-7-methoxy-4-oxo-1,4-dihydrobenzo[g]quinoline-3-carbonitrile as a yellow solid, mp>300° C.

$^1$HNMR ($d^6$-DMSO+trifluoroacetic acid): δ 8.67 (s, 1H); 8.64 (s, 1H); 7.84 (s, 1H); 7.57 (s, 1H); 7.29 (s, 1H); 3.98 (s, 3H).

MS (ES, positive ion mode): m/z calcd for $C_{15}H_{10}N_2O_3$: 266.3, found (M+H)$^+$ 266.8

Analysis for $C_{15}H_{10}N_2O_3$· 1.0 $(CH_3)_2NCHO$·0.8 $H_2O$ Calcd: C, 61.11; H, 5.30; N, 11.88. Found: C, 61.08; H, 4.81; N, 11.82.

EXAMPLE 14

4-Chloro-8-hydroxy-7-methoxybenzo[g]quinoline-3-carbonitrile

A mixture of 3.0 g (11.3 mmol) of 8-hydroxy-7-methoxy-4-oxo-1,4-dihydrobenzo[g]quinoline-3-carbonitrile and 20.0 mL of phosphorus oxychloride is heated under reflux for 0.5 hour, then is cooled to room temperature. Excess phosphorus oxychloride is evaporated to yield a residue, to which toluene is added and the resulting solution is reduced in vacuo. Toluene is added and evaporated twice more. The resulting residue is cooled with ice bath, neutralized with cold saturated solution of sodium bicarbonate and stirred. The solid was collected by filtration, is washed with cold water and is dried to yield 2.83 g of 4-chloro-8-hydroxy-7-methoxybenzo[g]quinoline-3-carbonitrile as a yellow solid. A sample of the material is purified by silica gel chromatography, eluting with 97:3 methylene chloride/methanol to yield a yellow solid, mp.>300° C.

$^1$HNMR ($d^6$-DMSO+trifluoroacetic acid): δ 8.68 (s, 1H); 8.64 (s, 1H); 7.83 (s, 1H); 7.58 (s, 1H); 7.27 (s, 1H); 3.96 (s, 3H).

MS (ES, positive ion mode): m/z calcd for $C_{15}H_9ClN_2O_2$: 284.7, found (M+H)$^+$ 284.7

Analysis for $C_{15}H_9ClN_2O_2$·0.6H$_2$O Calcd: C, 61.11; H, 5.30; N, 11.88. Found: C, 61.08; H, 4.81; N, 11.82.

EXAMPLE 15

4-[3-Chloro-4-(1-methyl-1H-imidazol-2-ylsulfanyl) phenylamino]-8-hydroxy-7-methoxybenzo[g]quinoline-3-carbonitrile A mixture of 1.0 g (3.53 mmol) of 4-chloro-8-hydroxy-7-methoxybenzo[g]quinoline-3-carbonitrile, 0.93 g (3.88 mmol) of 3-chloro-4-(1-methyl-1H-imidazol-2-ylsulfanyl)

phenylamine and 0.41 g (3.52 mmol) of pyridine hydrochloride in 20 mL of 2-ethoxyethanol is heated at 120° C. for 2 hours, then cooled to room temperature. The product mixture is diluted with a saturated solution of sodium carbonate, stirred for 15 minutes and the solid is collected by filtration. The solid is washed with water and dried in vacuo. The crude product is purified by silica gel chromatography, utilizing a 95:5 to 9:1 gradient of methylene chloride/methanol to give 1.13 g of 4-[3-chloro-4-(1-methyl-1H-imidazol-2-ylsulfanyl)phenylamino]-8-hydroxy-7-methoxybenzo[g]quinoline-3-carbonitrile as a yellow solid, mp>300° C.

$^1$HNMR (d$^6$-DMSO+trifluoroacetic acid): δ 9.22 (d, 2H, J=5.1); 8.28 (s, 1H); 8.06 (d, 1H, J=1.5 Hz); 7.98 (d, 1H, J=1.5 Hz); 7.92 (d, 1H, J=1.6 Hz); 7.58 (dd, 1H, J=1.7 Hz, J=8.07 Hz); 7.49 (s, 1H); 7.44 (s, 1H); (d, 1H, J=6.4 Hz); 4.05 (s, 3H); 3.88 (s, 3H).

MS (ES, positive ion mode): m/z calcd for $C_{25}H_{18}ClN_5O_2S$: 487.9, found (M+H)$^+$ 487.7

Analysis for $C_{25}H_{18}ClN_5O_2S.0.3H_2O$ Calcd: C, 60.86; H, 3.80; N, 14.20. Found: C, 60.82; H, 3.66; N, 14.03.

EXAMPLE 16

8-(2-Chloroethoxy)-4-[3-chloro-4-(1-methyl-1H-imidazol-2-ylsulfanyl)phenylamino]-7-methoxy-benzo[g]quinoline-3-carbonitrile A mixture of 0.8 g (1.64 mmol) of 4-[3-chloro-4-(1-methyl-1H-imidazol-2-ylsulfanyl)phenylamino]-8-hydroxy-7-methoxybenzo[g]quinoline-3-carbonitrile, 0.48 g (2.05 mmol) of 2-chloroethyl p-toluene sulfonate and 0.8 g (2.46 mmol) of cesium carbonate in 15 mL of dry dimethyl formamide was heated at 40° C. for 2 hours. To this was added 0.2 g (0.85 mmol) of 2-chloroethyl p-toluene sulfonate and 0.4 g (1.22 mmol) of cesium carbonate and the reaction mixture was further heated for 2 hours. After cooling to room temperature, the mixture was poured on to ice. The solid was collected by filtration, washed with water and ether, and dried to yield 1.0 g of dark yellow solid. A sample of the solid was purified by preparatory thin layer chromatography, eluting with 95:5% methylene chloride/methanol to give 8-(2-chloroethoxy)-4-[3-chloro-4-(1-methyl-1H-imidazol-2-ylsulfanyl)phenylamino]-7-methoxy-benzo[g]quinoline-3-carbonitrile as a yellow solid, mp. 275-280° C.

$^1$HNMR (d$^6$-DMSO+trifluoroacetic acid): δ 9.25 (d, 2H, J=7.3 Hz); 8.41 (s, 1H); 8.06 (d, 1H, J=1.5 Hz); 7.98 (d, 1H, J=1.5 Hz); 7.93 (d, 1H, J=1.7 Hz); 7.78 (s, 1H); 7.58 (dd, 1H, J=1.7 Hz, 9.9 Hz); 7.45 (s, 1H); 7.33 (d, 1H, J=6.4 Hz); 4.55 (t, 2H, J=3.6 Hz): 4.11 (t, 2H, J=3.9 Hz); 4.04 (s, 3H); 3.85 (s, 3H).

MS (ES, positive ion mode): m/z calcd for $C_{27}H_{21}Cl_2N_5O_2S$: 550.5, found (M+H)$^+$ 549.7

Analysis for $C_{27}H_{21}Cl_2N_5O_2S.1.7 H_2O$ Calcd: C, 55.80; H, 4.23; N, 12.05. Found: C, 56.05; H, 4.14; N, 11.70.

EXAMPLE 17

4-[3-Chloro-4-(1-methyl-1H-imidazol-2-ylsulfanyl)phenylamino]-7-methoxy-8-(2-morpholin-4-yl-ethoxy)benzo[g]quinoline-3-carbonitrile Procedure 1:

A mixture of 1.27 g (2.3 mmol) of 8-(2-chloroethoxy)-4-[3-chloro-4-(1-methyl-1H-imidazol-2-ylsulfanyl)phenylamino]-7-methoxybenzo[g]quinoline-3-carbonitrile, 4.0 mL of morpholine and 0.1 g of sodium iodide in 10 mL of 1,2-dimethoxyethane is heated under reflux for 16 hours. After allowing the reaction to cool, the solvent is evaporated to yield a residue, which is stirred with saturated sodium bicarbonate. The solid is collected by filtration, is washed with water and dried. The crude product is purified by silica gel chromatography, utilizing a gradient of 98:2 to 90:10 of methylene chloride/methanol to give 0.53 g of 4-[3-chloro-4-(1-methyl-1H-imidazol-2-ylsulfanyl)phenylamino]-7-methoxy-8-(2-morpholin-4-yl-ethoxy)benzo[g]quinoline-3-carbonitrile as a yellow solid, mp>300° C.

Procedure 2:

4-chloro-7-methoxy-8-(2-morpholin-4-yl-ethoxy)benzo[g]quinoline-3-carbonitrile

A mixture of 2.32 g (6.11 mmol) of 7-methoxy-8-(2-morpholin-4-yl-ethoxy)-4-oxo-1,4-dihydrobenzo[g]quinoline-3-carbonitrile and 35 mL of phosphorus oxychloride is heated under reflux for 1 hour, then cooled to room temperature. Excess phosphorus oxychloride is evaporated to yield a residue, to which toluene is added and the resulting solution is reduced in vacuo. Toluene is added and evaporated twice more. The resulting residue is cooled with ice bath, neutralized with cold saturated solution of sodium bicarbonate and stirred. The solid is collected by filtration, is washed with cold water and dried to yield 1.989 g of 4-chloro-7-methoxy-8-(2-morpholin-4-yl-ethoxy)benzo[g]quinoline-3-carbonitrile as a yellow solid.

MS (ES, positive ion mode): m/z calcd for $C_{21}H_{20}ClN_3O_4$397.9, found (M+H)$^+$ 398.2

A mixture of 1.98 g (4.98 mmol) of 4-chloro-7-methoxy-8-(2-morpholin-4-yl-ethoxy)benzo[g]quinoline-3-carbonitrile, 1.31 g (5.47 mmol) of 3-chloro-4(1-methyl-1H-imidazol-2-ylsulfanyl)phenylamine and 0.6 g (5.2 mmol) of pyridine hydrochloride in 2-ethoxyethanol is heated at 120° C. for 1.25 hours, then cooled. The crude mixture is poured into a solution of saturated sodium bicarbonate/ice and stirred for 45 minutes. The resulting solid is collected by filtration, then washed with water, ether and ethyl acetate successively. After drying in vacuo, the solid is purified by silica gel chromatography, using a 94:6 to 9:1 gradient of methylene chloride/methanol to provide a yellow solid. This solid is suspended in ether, filtered, and further washed with ether. After drying in vacuo, 1.77 g of 4-[3-chloro-4-(1-methyl-1H-imidazol-2-ylsulfanyl)phenylamino]-7-methoxy-8-(2-morpholin-4-yl-ethoxy)benzo[g]quinoline-3-carbonitrile is obtained as a yellow solid, mp.>300° C.

$^1$HNMR (d$^6$-DMSO+trifluoroacetic acid): δ 9.28 (s, 2H,); 8.45 (s, 1H); 8.06 (d, 1H, J=1.5 Hz); 7.98 (d, 1H, J=1.5 Hz); 7.93 (d, 1H, J=1.7 Hz); 7.83 (s, 1H); 7.58 (dd, 1H, J=1.7 Hz, 6.4 Hz); 7.48 (s, 1H); 7.35 (d, 1H, J=6.4 Hz); 4.67 (t, 2H, J=3.6 Hz); 4.06 (m, 2H); 4.04 (s, 3H); 3.87 (s, 3H); 3.77 (m, 4H); 3.67 (d, 2H, J=9.3 Hz); 3.36 (t, 2H, J=3.6 Hz).

MS (ES, positive ion mode): m/z calcd for $C_{31}H_{29}ClN_6O_3S$: 601.1, found (M+H)$^+$ 601.2

Analysis for $C_{31}H_{29}ClN_6O_3S.1.7 H_2O$ Calcd: C, 55.80; H, 4.23; N, 12.05. Found: C, 56.05; H, 4.14; N, 11.70.

EXAMPLE 18

4-[3-Chloro-4-(1-methyl-1H-imidazol-2-ylsulfanyl) phenylamino]-8-(3-chloropropoxy)-7-methoxybenzo [g]quinoline-3-carbonitrile Following the procedure of Example 16, 0.3 g (0.61 mmol) of 4-[3-chloro-4-(1-methyl-1H-imidazol-2-ylsulfanyl)phenylamino]-8-hydroxy-7-methoxybenzo[g]quinoline-3-carbonitrile is reacted with 0.19 g (0.77 mmol) of 3-chloropropyl p-toluene sulfonate and 0.3 g of (0.92 mmol) of cesium carbonate, then an additional 0.05 g (0.2 mmol) of 3-chloropropyl p-toluene sulfonate and 0.07 g (0.2 mmol) of cesium carbonate in 5 mL of dry dimethyl formamide to provide 0.3 g of a beige solid. A sample of the solid is purified by silica gel chromatography, utilizing a 99:1 to 95:5 gradient of methylene chloride/methanol to give 4-[3-chloro-4-(1-methyl-1H-imidazol-2-ylsulfanyl)phenylamino]-8-(3-chloropropoxy)-7-methoxybenzo[g]quinoline-3-carbonitrile as an orange solid, mp>300° C.

$^1$HNMR ($d^6$-DMSO+trifluoroacetic acid): δ 9.25 (d, 2H, J=8.6 Hz); 8.42 (s, 1H); 8.06 (d, 1H, J=1.5 Hz); 7.98 (d, 1H, J=1.5 Hz); 7.93 (d, 1H, J=1.7 Hz); 7.78 (s, 1H); 7.57 (dd, 1H, J=1.7 Hz, 6.4 Hz); 7.44 (s, 1H); 7.33 (d, 1H, J=6.4); 4.39 (t, 2H, J=4.5 Hz); 4.03 (s, 3H); 3.87 (m, 2H); 3.86 (s, 3H); 2.35 (m, 2H).

MS (ES, positive ion mode): m/z calcd for $C_{28}H_{23}Cl_2N_5O_2S$: 564.5, found (M+H)$^+$ 563.6

Analysis for $C_{28}H_{23}Cl_2N_5O_2S.2.0$ $H_2O$ Calcd: C, 56.51; H, 4.53; N, 11.66. Found: C, 56.51; H, 4.04; N, 11.37.

EXAMPLE 19

4-[3-Chloro-4-(1-methyl-1H-imidazol-2-ylsulfanyl) phenylamino]-7-methoxy-8-(3-morpholin-4-yl-propoxy)benzo[g]quinoline-3-carbonitrile Following procedure 1 of Example 17, a mixture of 0.13 g (0.22 mmol) of 4-[3-chloro-4-(1-methyl-1H-imidazol-2-ylsulfanyl)phenylamino]-8-(3-chloropropoxy)-7-methoxybenzo[g]quinoline-3-carbonitrile, 0.3 mL of morpholine and 0.01 g of sodium iodide is heated under reflux for 16 hours, to provide 0.054 g of a yellow solid. A sample of the solid is purified by silica gel chromatography, utilizing a 97:3 to 90:10 gradient of methylene chloride/methanol to give 4-[3-chloro-4-(1-methyl-1H-imidazol-2-ylsulfanyl)phenylamino]-7-methoxy-8-(3-morpholin-4-yl-propoxy)benzo[g]quinoline-3-carbonitrile as a yellow solid, mp 230-235° C.

$^1$HNMR ($d^6$-DMSO+trifluoroacetic acid): δ 9.26 (s, 2H,); 8.42 (s, 1H); 8.05 (d, 1H, J=1.2 Hz); 7.97 (d, 1H, J=1.2 Hz); 7.92 (d, 1H, J=1.6 Hz); 7.73 (s, 1H); 7.57 (dd, 1H, J=1.6 Hz, 6.3 Hz); 7.46 (s, 1H); 7.33 (d, 1H, J=6.4 Hz); 4.36 (t, 2H, J=3.6 Hz); 4.07 (m, 2H); 4.02 (s, 3H); 3.85 (s, 3H); 3.71 (t, 2H, J=9.1 Hz); 3.58 (d, 2H, J=9.1 Hz); 3.38 (t, 2H, J=5.4 Hz); 3.19 (t, 2H, J=8.0 Hz); 2.33 (m, 2H).

MS (ES, positive ion mode): m/z calcd for $C_{32}H_{31}ClN_6O_3S$: 615.2, found (M+H)$^+$ 614.7

Analysis for $C_{32}H_{31}ClN_6O_3S.1.5$ $H_2O$ Calcd: C, 59.85; H, 5.34; N, 13.09. Found: C, 59.78; H, 5.04; N, 12.98.

EXAMPLE 20

4-[3-Chloro-4-(1-methyl-1H-imidazol-2-ylsulfanyl) phenylamino]-7-methoxy-8-[2-(4-methylpiperazin-1-yl)ethoxy]-benzo[g]quinoline-3-carbonitrile Following procedure 1 of Example 17, a mixture of 0.15 g (0.3 mmol) of 8-(2-chloroethoxy)-4-[3-chloro-4-(1-methyl-1H-Imidazol-2-ylsulfanyl)phenylamino]-7-methoxybenzo[g]quinoline-3-carbonitrile, 0.5 mL of 1-methylpiperazine and 0.02 g of sodium iodide is heated under reflux for 16 hours. Purification of the material is carried out by silica gel flash chromatography, utilizing a 90:10 to 85:15 gradient of methylene chloride/methanol to give 0.052 g of 4-[3-chloro-4-(1-methyl-1H-imidazol-2-ylsulfanyl)phenylamino]-7-methoxy-8-[2-(4-methylpiperazin-1-yl)ethoxy]-benzo[g]quinoline-3-carbonitrile as a yellow solid, mp 184-186° C.

$^1$HNMR ($d^6$-DMSO+trifluoroacetic acid): δ 9.28 (d, 2H, J=1.9 Hz); 8.45 (s, 1H); 8.06 (d, 1H, J=1.4 Hz); 7.8 (d, 1H, J=1.4 Hz); 7.93 (d, 1H, J=1.7 Hz); 7.82 (s, 1H); 7.57 (dd, 1H, J=1.7 Hz, 6.4 Hz); 7.49 (s, 1H); 7.34 (d, 1H, J=6.4 Hz); 4.67 (m, 2H); 4.03 (s, 3H); 3.89 (m, 2H); 3.86 (s, 3H); 3.71-3.25 (m, 6H); 3.2 (m, 2H); 2.97 (s, 3H).

MS (ES, positive ion mode): m/z calcd for $C_{32}H_{32}ClN_7O_2S$: 614.2, found (M+2H)$^{2+}$ 307.6

Analysis for $C_{32}H_{32}ClN_7O_2S.3.5$ $H_2O$ Calcd: C, 56.74; H, 5.80; N, 14.48. Found: C, 56.57; H, 5.46; N, 14.12.

EXAMPLE 21

4-[3-Chloro-4-(1-methyl-1H-imidazol-2-ylsulfanyl) phenylamino]-7-methoxy-8-(2-[1,2,3]triazol-2-yl-ethoxy)benzo[g]quinoline-3-carbonitrile And

EXAMPLE 22

4-[3-Chloro-4-(1-methyl-1H-imidazol-2-ylsulfanyl) phenylamino]-7-methoxy-8-(2-[1,2,3]triazol-1-yl-ethoxy)benzo[g]quinoline-3-carbonitrile A mixture of 0.3 g (0.55 mmol) of 8-(2-chloroethoxy)-4-[3-chloro-4-(1-methyl-1H-imidazol-2-ylsulfanyl)phenylamino]-7-methoxybenzo[g]quinoline-3-carbonitrile, 0.32 mL (5.5 mmol) of 1H-1,2,3-triazole and 0.1 g (2.5 mmol) of sodium hydroxide powder in 5 mL of N,N-dimethyl formamide is heated at 80° C. for 4.5 hours, then cooled and poured on to ice. The solid is collected by filtration, washed with water and dried. The two isomers are separated by silica gel chromatography, utilizing a 99:1 to 85:15 gradient of ethyl acetate/methanol. The less polar material, 0.062 g of 4-[3-chloro-4-(1-methyl-1H-imidazol-2-ylsulfanyl)phenylamino]-7-methoxy-8-(2-[1,2,3]triazol-2-yl-ethoxy)benzo [g]quinoline-3-carbonitrile is obtained as yellow solid, mp 235-237° C.

$^1$HNMR ($d^6$-DMSO+trifluoroacetic acid): δ 9.22 (d, 2H, J=11.5 Hz); 8.4 (s, 1H); 8.04 (d, 1H, J=1.4 Hz); 7.96 (d, 1H, J=1.4 Hz); 7.92 (d, 1H, J=1.7 Hz); 7.81 (m, 3H); 7.55 (dd, 1H, J=1.7 Hz, 6.4 Hz); 7.43 (s, 1H); 7.30 (d, 1H, J=6.4 Hz); 4.98 (t, 2H, J=3.8 Hz); 4.79 (t, 2H, J=3.8 Hz); 3.96 (s, 3H); 3.84 (s, 3H).

MS (ES, positive ion mode): m/z calcd for $C_{29}H_{23}ClN_8O_2S$: 583.1, found (M+H)$^+$ 582.7

Analysis for $C_{29}H_{23}ClN_8O_2S.1$ $H_2O$ Calcd: C, 57.94; H, 4.19; N, 18.64. Found: C, 57.73; H, 4.10; N, 18.65.

The more polar material, 0.087 g of 4-[3-chloro-4-(1-methyl-1H-imidazol-2-ylsulfanyl)phenylamino]-7-methoxy-8-(2-[1,2,3]triazol-1-yl-ethoxy)benzo[g]quinoline-3-carbonitrile, is obtained as an orange solid, mp 201-207° C.

$^1$HNMR ($d^6$-DMSO+trifluoroacetic acid): δ 9.24 (d, 2H, J=8.9 Hz); 8.4 (s, 1H); 8.24 (s, 1H); 8.06 (d, 1H, J=1.2 Hz); 7.98 (d, 1H, J=1.2 Hz); 7.93 (d, 1H, J=1.5 Hz); 7.78 (s, 1H, J=5.1 Hz); 7.57 (dd, 1H, J=1.5 Hz, 6.3 Hz); 7.43 (s, 1H); 7.33 (d, 1H, J=6.4 Hz); 4.99 (t, 2H, J=4.0 Hz); 4.71 (t, 2H, J=3.6 Hz); 4.00 (s, 3H); 3.86 (s, 3H).

MS (ES, positive ion mode): m/z calcd for C$_{29}$H$_{23}$ClN$_8$O$_2$S: 583.1, found (M+H)$^+$ 582.7

Analysis for C$_{29}$H$_{23}$ClN$_8$O$_2$S.2 H$_2$O Calcd: C, 56.26; H, 4.40; N, 18.10. Found: C, 56.34; H, 4.19; N, 17.83.

EXAMPLE 23

4-(2,4-Dichloro-5-methoxyphenylamino)-8-hydroxy-7-methoxybenzo[g]quinoline-3-carbonitrile A mixture of 0.7 g (2.46 mmol) of 4-chloro-8-hydroxy-7-methoxybenzo[g]quinoline-3-carbonitrile, 0.57 g (2.95 mmol) of 2,4-dichloro-5-methoxyaniline and 0.28 g (2.46 mmol) of pyridine hydrochloride in 7 mL of 2-ethoxyethanol is heated at 120° C. for 2 hours, then cooled to room temperature. The product mixture is diluted with saturated solution of sodium bicarbonate and stirred for 15 minutes. The resulting solid is collected by filtration, washed with water and dried. The crude product is purified by silica gel chromatography, utilizing a 98:2 to 90:10 gradient of methylene chloride/methanol to give 0.71 g of 4-(2,4-dichloro-5-methoxyphenylamino)-8-hydroxy-7-methoxybenzo[g]quinoline-3-carbonitrile as a yellow solid, mp, 238-240° C.

$^1$HNMR (d$^6$-DMSO+trifluoroacetic acid): δ 9.31 (s, 1H); 9.22 (s, 1H); 8.28 (s, 1H); 7.89 (s, 1H); 7.64 (s, 1H); 7.44 (s, 1H); 7.41 (s, 1H); 4.03 (s, 3H); 3.91 (s, 3H);

MS (ES, positive ion mode): m/z calcd for C$_{22}$H$_{15}$Cl$_2$N$_3$O$_3$: 440.3, found (M+H)$^+$ 439.7

Analysis for C$_{22}$H$_{15}$Cl$_2$N$_3$O$_3$.1.0 H$_2$O Calcd: C, 57.65; H, 3.74; N, 9.17. Found: C, 57.80; H, 3.94; N, 8.82.

EXAMPLE 24

8-(3-Chloropropoxy)-4-(2,4-dichloro-5-methoxyphenylamino)-7-methoxybenzo[g]quinoline-3-carbonitrile Following the procedure of Example 16, 0.43 g (0.98 mmol) of 4-(2,4-dichloro-5-methoxyphenylamino)-8-hydroxy-7-methoxybenzo[g]quinoline-3-carbonitrile is reacted with 0.31 g (1.25 mmol) of 3-chloropropyl p-toluene sulfonate and 0.48 g of (1.47 mmol) of cesium carbonate, then an additional 0.05 g (0.2 mmol) of 3-chloropropyl p-toluene sulfonate and 0.07 g (0.2 mmol) of cesium carbonate in 6 mL of dry dimethyl formamide. The crude product is purified by silica gel flash chromatography, utilizing a 99.5:0.5 to 99:1 gradient of methylene chloride/methanol to give 0.118 g of 8-(3-chloropropoxy)-4-(2,4-dichloro-5-methoxyphenylamino)-7-methoxybenzo[g]quinoline-3-carbonitrile as a yellow solid, mp 220-223° C.

$^1$HNMR (d$^6$-DMSO+trifluoroacetic acid): δ 9.35 (s, 1H); 9.25 (s, 1H); 8.44 (s, 1H); 7.87 (s, 1H); 7.77 (s, 1H); 7.61 (s, 1H); 7.47 (s, 1H); 4.41 (t, 2H, J=4.5 Hz); 4.06 (s, 3H); 3.93 (s, 3H); 3.88 (t, 2H, J=4.8 Hz); 2.35 (m, 2H).

MS (ES, positive ion mode): m/z calcd for C$_{25}$H$_{20}$Cl$_3$N$_3$O$_3$: 516.8, found (M+H)$^+$ 517.6

Analysis for C$_{25}$H$_{20}$Cl$_3$N$_3$O$_3$.0.5 H$_2$O Calcd: C, 57.10; H, 4.03; N, 7.99. Found: C, 57.01; H, 4.00; N, 7.86.

EXAMPLE 25

4-(2,4-Dichloro-5-methoxyphenylamino)-7-methoxy-8-(3-morpholin-4-yl-propoxy)benzo[g]quinoline-3-carbonitrile Following procedure 1 of Example 17, a mixture of 0.105 g (0.20 mmol) of 8-(3-chloropropoxy)-4-(2,4-dichloro-5-methoxyphenylamino)-7-methoxybenzo[g]quinoline-3-carbonitrile, 0.3 mL of morpholine and 0.01 g of sodium iodide in 10 mL of 1,2-dimethoxyethane is heated under reflux for 7 hours. The resulting solid is purified by silica gel chromatography, utilizing a 98:2 to 94:6 gradient of methylene chloride/methanol to give 0.089 g of 4-(2,4-dichloro-5-methoxyphenylamino)-7-methoxy-8-(3-morpholin-4-yl-propoxy)benzo[g]quinoline-3-carbonitrile as a yellow solid, mp 205-208° C.

$^1$HNMR (d$^6$-DMSO+trifluoroacetic acid): δ 9.37 (s, 1H); 9.26 (s, 1H); 8.44 (s, 1H); 7.88 (s, 1H); 7.73 (s, 1H); 7.63 (s, 1H); 7.49 (s, 1H); 4.39 (t, 2H, J=5.5 Hz); 4.09 (m, 2H); 4.05 (s, 3H); 3.93 (s, 3H); 3.75 (t, 2H, J=11.7 Hz); 3.60 (d, 2H, J=12.2 Hz); 3.42 (t, 2H, J=7.0 Hz); 3.21 (t, 2H, J=9.3 Hz); 2.35 (m, 2H).

MS (ES, positive ion mode): m/z calcd for C$_{29}$H$_{28}$Cl$_2$N$_4$O$_4$: 567.5, found (M+H)$^+$ 566.7

Analysis for C$_{29}$H$_{28}$Cl$_2$N$_4$O$_4$.1.7 H$_2$O Calcd: C, 58.23; H, 5.29; N, 9.37. Found: C, 57.91; H, 5.15; N, 9.12.

EXAMPLE 26

4-(2,4-Dichloro-5-methoxyphenylamino)-7-methoxy-8-(2-[1,2,3]triazol-2-yl-ethoxy)benzo[g]quinoline-3-carbonitrile And

EXAMPLE 27

4-(2,4-Dichloro-5-methoxyphenylamino)-7-methoxy-8-(2-[1,2,3]triazol-1-yl-ethoxy)benzo[g]quinoline-3-carbonitrile Following the procedure of Example 16, 0.28 g (0.64 mmol) of 4-(2,4-dichloro-5-methoxyphenylamino)-8-hydroxy-7-methoxybenzo[g]quinoline-3-carbonitrile is reacted with 0.18 g (0.76 mmol) of 2-chloroethyl p-toluene sulfonate and 0.3 g of (0.92 mmol) of cesium carbonate, then an additional 0.05 g (0.2 mmol) of 2-chloroethyl p-toluene sulfonate and 0.07 g (0.2 mmol) of cesium carbonate in 5 mL of dry dimethyl formamide. This provides 0.31 g of 8-(2-chloroethoxy)-4-(2,4-dichloro-5-methoxyphenylamino)-7-methoxybenzo[g]quinoline-3-carbonitrile as a brown solid.

MS (ES, positive ion mode): m/z calcd for C$_{28}$H$_{22}$Cl$_2$N$_5$O$_2$S: 502.8, found (M+H)$^+$ 503.7

A mixture of 0.31 g (0.62 mmol) of 8-(2-chloroethoxy)-4-(2,4-dichloro-5-methoxyphenylamino)-7-methoxybenzo[g]quinoline-3-carbonitrile, 0.36 mL (6.1 mmol) of 1H-1,2,3-triazole and 0.11 g (2.8 mmol) of sodium hydroxide powder in 5 mL of N,N-dimethyl formamide is heated at 80° C. for 4.5 hours, then cooled and poured on to ice. The solid is collected by filtration, washed with water and dried. The two isomers are separated by silica gel flash chromatography, using first 7:3 ethyl acetate/hexane, then a 100:0 to 9:1 gradient of ethyl acetate/methanol. The less polar material, 0.071 g of 4-(2,4-dichloro-5-methoxyphenylamino)-7-methoxy-8-(2-[1,2,3]triazol-2-yl-ethoxy)benzo[g]quinoline-3-carbonitrile, is obtained as yellow solid, mp 285-287° C.

$^1$HNMR (d$^6$-DMSO+trifluoroacetic acid): δ 9.34 (s, 1H); 9.22 (s, 1H); 8.44 (s, 1H); 7.84 (s, 1H); 7.79 (s, 2H); 7.77 (s, 1H); 7.60 (s, 1H); 7.46 (s, 1H); 5.01 (t, 2H, J=3.8 Hz); 4.84 (t, 2H, J=3.7 Hz); 4.00 (s, 3H); 3.94 (s, 3H).

MS (ES, positive ion mode): m/z calcd for C$_{26}$H$_{20}$Cl$_2$N$_6$O$_3$: 535.4, found (M+H)$^+$ 534.6

Analysis for C$_{26}$H$_{20}$Cl$_2$N$_6$O$_3$.0.5 H$_2$O Calcd: C, 57.36; H, 3.89; N, 15.44. Found: C, 57.45; H, 3.86; N, 15.14.

The more polar material, 0.053 g of 4-(2,4-dichloro-5-methoxyphenylamino)-7-methoxy-8-(2-[1,2,3]triazol-1-ylethoxy)benzo[g]quinoline-3-carbonitrile, is obtained as brown solid, mp 245° C. (dec).

$^1$HNMR (d$^6$-DMSO+trifluoroacetic acid): δ 9.35 (s, 1H); 9.27 (s, $_1$H); 8.42 (s, 1H); 8.25 (d, 1H, J=0.6 Hz); 7.89 (s, 1H); 7.79 (d, 2H, J=3.3 Hz); 7.64 (s, 1H); 7.44 (s, 1H); 5.0 (t, 2H, J=3.8 Hz); 4.72 (t, 2H, J=3.7 Hz); 4.03 (s, 3H); 3.91 (s, 3H).

MS (ES, positive ion mode): m/z calcd for $C_{28}H_{20}Cl_2N_6O_3$: 535.4, found (M+H)$^+$ 534.6

Analysis for $C_{26}H_{20}Cl_2N_6O_3 \cdot 1.3H_2O$ Calcd: C, 55.88; H, 4.08; N, 15.04. Found: C, 55.97; H, 4.05; N, 14.86.

EXAMPLE 28

3-Amino-3-(4-benzyloxy-3-methoxy-7-phenylsulfanylbicyclo[4.2.0]octa-1,3,5-trien-7-yl)acrylonitrile To a stirred solution of ethylmagnesium bromide (3.0 mL of a 3M solution in diethyl ether, 9.0 mmol) in anhydrous tetrahydrofuran (10 mL) at 0° C. under nitrogen is added diisopropylamine (2.5 mL, 17.8 mmol). The mixture is stirred at 0° C. for 1 hour and acetonitrile (0.25 mL, 4.8 mmol) and a solution of 4-benzyloxy-3-methoxy-7-phenylsulfanylbicyclo[4.2.0]octa-1,3,5-triene-7-carbonitrile (0.83 g, 2.2 mmol) in anhydrous tetrahydrofuran (3 mL) are added successively, and the resulting mixture is stirred for an additional hour. The reaction is quenched with aqueous ammonium chloride and the product is extracted with ethyl acetate. The extract is washed with brine, dried over anhydrous sodium sulfate and evaporated to yield a solid. The crude product is purified by silica gel chromatography, utilizing a 9:1 to 4:1 gradient of hexane/ethyl acetate to yield 0.527 g of 3-amino-3-(4-benzyloxy-3-methoxy-7-phenylsulfanylbicyclo[4.2.0]octa-1,3,5-trien-7-yl)acrylonitrile as a white solid, mp 122-125° C.

$^1$HNMR (d$^6$-DMSO+trifluoroacetic acid): δ 7.43-7.37 (m, 5H); 7.35-7.31 (m, 5H); 6.81 (s, 1H); 6.64 (s, 2H); 6.61 (s, 1H); 5.00 (d, 1H, J=12.1 Hz); 4.94 (d, 1H, J=12.1 Hz); 3.72 (s, 3H); 3.57 (s, 1H); 3.49 (d, 1H, J=14.0 Hz); 3.29 (d, 1H, J=13.0 Hz).

MS (ES, positive ion mode): m/z calcd for $C_{25}H_{22}N_2O_2S$: 414.5, found (M+H)$^+$ 414.8

Analysis for $C_{25}H_{22}N_2O_2S \cdot 0.3 H_2O$ Calcd: C, 71.50; H, 5.42; N, 6.67. Found: C, 71.51; H, 5.28; N, 6.56.

EXAMPLE 29

3-Amino-6-benzyloxy-7-methoxynaphthalene-2-carbonitrile

Nitrogen gas is bubbled through a solution of 3-amino-3-(4-benzyloxy-3-methoxy-7-phenylsulfanylbicyclo[4.2.0]octa-1,3,5-trien-7-yl)acrylonitrile (0.39 g, 0.93 mmol) in 1,2-dichlorobenzene (500 mL) for 1 hour and the reaction is heated to 179° C. After 2.5 hours the reaction was cooled down and reduced in vacuo. The residue was washed with ether, dissolved in methylene chloride and purified through a plug of silica. The filtrate is reduced and dried to afford 0.19 g of 3-amino-6-benzyloxy-7-methoxynaphthalene-2-carbonitrile as a yellow solid, mp 241-243° C.

$^1$HNMR (d$^6$-DMSO+trifluoroacetic acid): δ 7.98 (s, 1H); 7.61-7.44 (m, 2H); 7.40-7.34 (m, 3H); 7.17 (s, 1H); 7.11 (s, 1H); 6.94 (s, 1H); 5.64 (s, 2H); 5.19 (s, 2H); 3.81 (s, 3H).

MS (ES, positive ion mode): m/z calcd for $C_{19}H_{16}N_2O_2$: 304.3, found (M−H)+ 304.8

Analysis for $C_{19}H_{16}N_2O_2 \cdot 0.6 H_2O$ Calcd: C, 72.40; H, 5.50; N, 8.89. Found: C, 72.40; H, 5.34; N, 8.78.

EXAMPLE 30

(8-Benzyloxy-7-methoxybenzo[g]quinazolin-4-yl)-(2,4-dichloro-5-methoxyphenyl)amine A mixture of 0.12 g (1.7 mmol) of 3-amino-6-benzyloxy-7-methoxynaphthalene-2-carbonitrile and 0.5 mL of N,N-dimethylformamide dimethyl acetal in 2.0 mL of toluene is heated under reflux for 4 hours. The solvent is evaporated and the residue is dried on high vacuum to yield N'-(7-benzyloxy-3-cyano-6-methoxynaphthalen-2-yl)-N,N-dimethylformamidine as an off-white solid.

A mixture of N'-(7-benzyloxy-3-cyano-6-methoxynaphthalen-2-yl)-N,N-dimethylformamidine and 0.092 g (0.48 mmol) of 2,4-dichloro-5-methoxyaniline in 4 mL of glacial acetic acid is heated under reflux for 7 hours, then cooled to room temperature and stirred overnight. The resulting solid is collected by filtration, washed with ether and dried to yield 0.05 g of (8-benzyloxy-7-methoxybenzo[g]quinazolin-4-yl)-(2,4-dichloro-5-methoxyphenyl)amine as a yellow solid, mp 275-280° C.

$^1$HNMR (d$^6$-DMSO+trifluoroacetic acid): δ 9.25 (s, 1H); 8.95 (s, 1H); 8.28 (s, 1H); 7.86 (s, 2H); 7.59-7.39 (m, 7H); 5.37 (s, 2H); 4.04 (s, 3H); 3.90 (s, 3H).

MS (ES, positive ion mode): m/z calcd for $C_{27}H_{21}Cl_2N_3O_3$: 506.4, found (M−H)$^+$ 505.7

Analysis for $C_{27}H_{21}Cl_2N_3O_3 \cdot 0.5 H_2O$ Calcd: C, 62.91; H, 4.30; N, 8.15. Found: C, 62.95; H, 4.45; N, 7.85.

EXAMPLE 31

4-Chloro-7-methoxy-8-(2-morpholin-4-yl-ethoxy)benzo[g]quinazoline

A mixture of 0.3 g (0.844 mmol) of 7-methoxy-8-(2-morpholin-4-yl-ethoxy)-3H-benzo[g]quinazolin-4-one in 8 mL of phosphorus oxychloride and 1 mL of diethylaniline is refluxed for 15 minutes. After allowing to cool to room temperature, phosphorus oxychloride and diethylaniline are removed in vacuo. A 5 mL portion of toluene is added to the crude product mixture, and the solvents are again removed in vacuo. This step is repeated one more time. The product mixture is placed in an ice bath, and to this is added 10 mL of an ice-cooled solution of saturated sodium bicarbonate. This is extracted twice with a 95:5 mixture of methylene chloride/methanol, then with 1:1 tetrahydrofuran/ethyl acetate. The organic layers are combined, dried over magnesium sulfate and concentrated in vacuo. Purification by silica gel chromatography, eluting with a solvent gradient of 98:2 to 4:1 methylene chloride/methanol, provided 0.229 g of 4-chloro-7-methoxy-8-(2-morpholin-4-yl-ethoxy)benzo[g]quinazoline as a yellow solid, mp 166-168° C.

$^1$HNMR (d$^6$-DMSO): δ 8.97 (s, 1H); 8.78 (s, 1H); 8.50 (s, 1H); 7.75 (s, 1H); 7.68 (s, 1H); 4.32 (t, 2H, J=4.4 Hz); 3.98 (s, 3H); 3.61 (t, 4H, J=3.5 Hz); 2.83 (t, 2H, J=4.3 Hz); 2.54 (m, 4H).

MS (ES, positive ion mode): m/z calcd for $C_{19}H_{20}ClN_3O_3$: 373.8, found (M+H)$^+$ 374.2

Analysis for $C_{19}H_{20}ClN_3O_3$ Calcd: C, 61.04; H, 5.39; N, 11.24. Found: C, 60.92; H, 5.16; N, 10.98.

EXAMPLE 32

(4-Bromo-2-fluorophenyl)-[7-methoxy-8-(2-morpholin-4-yl-ethoxy)benzo[g]quinazolin-4-yl]-amine To a suspension of 0.1 g (0.267 mmol) of 4-chloro-7-methoxy-8-(2-morpholin-4-yl-ethoxy)benzo[g]quinazoline in 3 mL of ethanol is added 0.061 g (0.321 mmol) of 4-bromo-2-fluoroaniline and 0.031 g (0.267 mmol) of pyridine hydrochloride. The mixture is brought to reflux for 55 minutes, then allowed to cool to room temperature. A yellow precipitate formed, which is filtered and washed with cold ethanol. Drying in vacuo provided 0.103 g of (4-bromo-2-fluorophenyl)-[7-methoxy-8-(2-morpholinyl-4-yl-ethoxy)benzo[g]quinazolin-4-yl]-amine dihydrochloride as a yellow solid, mp 210-225° C.

$^1$HNMR (d$^6$-DMSO+trifluoroacetic acid): δ 12.02 (broad s, 1H); 11.45 (broad s, 1H); 9.36 (s, 1H); 8.88 (s, 1H); 8.33 (s, 1H); 7.84 (s, 1H); 7.80 (s, 1H); 7.60 (s, 2H); 7.44 (s, 1H); 4.71 (m, 2H); 4.02 (s, 3H); 3.99 (m, 2H); 3.86 (m, 2H); 3.70 (m, 2H); 3.58 (m, 2H); 3.46 (m, 2H).

MS (ES, positive ion mode): m/z calcd for $C_{25}H_{24}BrFN_4O_3$: 527.4, found (M+H)$^+$ 528.7

Analysis for $C_{25}H_{24}BrFN_4O_3.2HCl.CH_3CH_2OH$ Calcd: C, 50.17; H, 4.99; N, 8.67. Found: C, 50.23; H, 4.91; N, 8.32.

EXAMPLE 33

(2,4-Dichloro-5-methoxyphenyl)-[7-methoxy-8-(2-morpholin-4-yl-ethoxy)benzo[g]quinazolin-4-yl]-amine To a suspension of 0.05 g (0.133 mmol) of 4-chloro-7-methoxy-8-(2-morpholin-4-yl-ethoxy)benzo[g]quinazoline in 2 mL of isopropanol is added 0.031 g (0.161 mmol) of 2,4-dichloro-5-methoxyaniline and 0.016 g (0.133 mmol) of pyridine hydrochloride. The mixture is brought to reflux for 2 hours, then allowed to cool to room temperature. A yellow precipitate formed, which is filtered and washed with cold isopropanol. Drying in vacuo provided 0.030 g of (2,4-dichloro-5-methoxyphenyl)-[7-methoxy-8-(2-morpholin-4-yl-ethoxy)benzo[g]quinazolin-4-yl]-amine dihydrochloride as a yellow solid, mp 258-260° C.

$^1$HNMR (d$^6$-DMSO+trifluoroacetic acid): δ 9.29 (s, 1H); 8.96 (s, 1H); 8.32 (s, 1H); 7.84 (s, 1H); 7.82 (s, 1H); 7.51 (s, 2H); 4.68 (m, 2H); 4.06 (s, 3H); 3.98 (m, 2H); 3.91 (s, 3H); 3.79-3.73 (m, 4H); 3.70-3.67 (m, 2H); 3.40-3.33 (m, 2H).

MS (ES, positive ion mode): m/z calcd for $C_{26}H_{26}Cl_2N_4O_4$: 529.4, found (M+H)$^+$ 528.8

Analysis for $C_{26}H_{26}Cl_2N_4O_4.2HCl.4H_2O$ Calcd: C, 46.31; H, 5.38; N, 8.31. Found: C, 46.37; H, 5.17; N, 8.23.

EXAMPLE 34

(3-Bromophenyl)-[7-methoxy-8-(2-morpholin-4-yl-ethoxy)benzo[g]quinazolin-4-yl]-amine To a suspension of 0.1 g (0.267 mmol) of 4-chloro-7-methoxy-8-(2-morpholin-4-yl-ethoxy)benzo[g]quinazoline in 3 mL of isopropanol is added 0.055 g (0.321 mmol) of 3-bromoaniline and 0.031 g (0.267 mmol) of pyridine hydrochloride. The mixture is brought to reflux for 15 minutes, then allowed to cool to room temperature. A yellow precipitate forms, which is filtered and washed with cold ethanol. Drying in vacuo provided 0.131 g of (3-bromophenyl)-[7-methoxy-8-(2-morpholin-4-yl-ethoxy)benzo[g]quinazolin-4-yl]-amine dihydrochloride as a yellow solid, mp 266-269° C.

$^1$HNMR (d$^6$-DMSO+trifluoroacetic acid): δ 9.36 (s, 1H); 9.07 (d, 1H, J=1.4 Hz); 8.31 (s, 1H); 8.19 (d, 1H, J=1.2 Hz); 7.87 (d, 1H, J=5.3 Hz); 7.82 (s, 1H); 7.59 (d, 1H, J=6 Hz); 7.53 (dd, 1H, J=1.8 Hz, J=5.9 Hz); 7.50 (s, 1H); 4.70 (m, 2H); 4.06 (s, 3H); 4.04 (m, 2H); 3.84-3.78 (m, 4H); 3.70-3.67 (m, 2H); 3.36 (t, 2H, J=6.8 Hz).

MS (ES, positive ion mode): m/z calcd for $C_{25}H_{25}BrN_4O_3$: 509.4, found (M+H)$^+$ 509.1

Analysis for $C_{25}H_{25}BrN_4O_3.2HCl.2.5H_2O$ Calcd: C, 47.86; H, 5.14; N, 8.93. Found: C, 47.68; H, 4.98; N, 8.82.

What is claimed is:

1. A process for the production of 6,7,8-substituted 3-amino-2-naphthoates or 3-amino-2-naphthonitriles of formula (A)

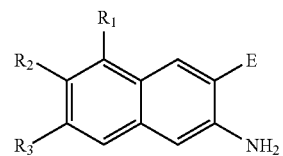

A wherein
- E is cyano or E is an alkoxycarbonyl of 2-12 carbons, —$CO_2$-Ph, —$CO_2$-L, cycloalkoxycarbonyl of 4-12 carbons, alkenyloxycarbonyl of 3-12 carbons, cycloalkenyloxycarbonyl of 5-12 carbons, alkynyloxycarbonyl of 4-12 carbons, any of which may be substituted on a carbon atom with one or more $R_6$ groups;
- $R_1$, $R_2$ and $R_3$ are each, independently, hydrogen, halogen, hydroxy, amino, hydroxyamino, trifluoromethyl, trifluoromethoxy, mercapto, alkyl of 1-6 carbon atoms, cycloalkyl of 3-8 carbon atoms, alkenyl of 2-6 carbon atoms, alkynyl of 2-6 carbon atoms, alkenyloxy of 2-6 carbon atoms, alkynyloxy of 2-6 carbon atoms, hydroxyalkyl of 1-6 carbon atoms, mercaptoalkyl of 1-6 carbon atoms, halomethyl, alkoxymethyl of 2-7 carbon atoms, alkoxy of 1-6 carbon atoms, cycloalkoxy of 3-8 carbon atoms, alkylthio of 1-6 carbon atoms, cycloalkylthio of 3-8 carbon atoms, alkylsulphinyl of 1-6 carbon atoms, alkylsulfonyl of 1-6 carbon atoms, alkylsulfonamido of 1-6 carbon atoms, alkenylsulfonamido of 2-6 carbon atoms, alkynylsulfonamido of 2-6 carbon atoms, cyano, nitro, carboxy, alkoxycarbonyl of 2-7 carbon atoms, alkanoyl of 2-7 carbon atoms, alkenoyl of 3-7 carbon atoms, N-alkyl-N-alkenylamino of 4 to 12 carbon atoms, N,N-dialkenylamino of 6-12 carbon atoms, phenylamino, benzylamino, phenoxy, phenyl, thiophenoxy, benzyl, alkylamino of 1-6 carbon atoms, alkanoyloxy of 2-7 carbon atoms, alkenoyloxy of 3-8 carbon atoms, alkynoyloxy of 3-8 carbon atoms, carbamoyl, N-alkylcarbamoyl of 2-7 carbon atoms, N,N-dialkylcarbamoyl of 3-13 carbon atoms, dialkylamino of 2 to 12 carbon atoms, alkanoyloxymethyl group of 2-7 carbon atoms, alkenoyloxymethyl group of 2-7 carbon atoms, alkynoyloxymethyl group of 2-7 carbon atoms, azido, benzoyl, carboxyalkyl of 2-7 carbons, carboalkoxyalkyl of 3-8 carbon atoms,

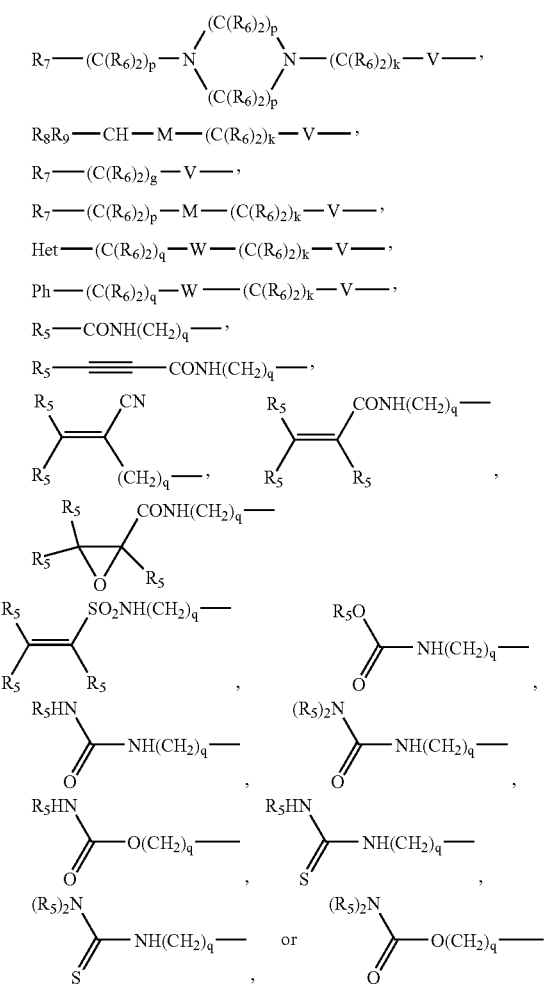

R$_5$ is independently hydrogen, alkyl of 1-6 carbon atoms, aminoalkyl of 1-6 carbon atoms, N-alkylaminoalkyl of 2-9 carbon atoms, N,N-dialkylaminoalkyl of 3-12 carbon atoms, N-cycloalkylaminoalkyl of 4-12 carbon atoms, N-cycloalkyl-N-alkylaminoalkyl of 5-18 carbon atoms, N,N-dicycloalkylaminoalkyl of 7-18 carbon atoms, morpholino-N-alkyl wherein the alkyl group is 1-6 carbon atoms, piperidino-N-alkyl wherein the alkyl group is 1-6 carbon atoms, N-alkyl-piperazino-N-alkyl wherein either alkyl group is 1-6 carbon atoms, azacycloalkyl-N-alkyl of 3-11 carbon atoms, hydroxyalkyl of 1-6 carbon atoms, alkoxyalkyl of 2-8 carbon atoms, phenyl;

V is $(CH_2)_m$, O, S, or $NR_6$;

R$_7$ is $NR_6R_6$, $OR_6$, J, $N(R_6)_3^+$, or $NR_6(OR_6)$;

M is $NR_6$, O, S, $N-[(C(R_6)_2)_p NR_6R_6]$, or $N-[(C(R_6)_2)_p-OR_6]$;

W is $NR_6$, O, S, or is a bond;

Het is a heterocycle selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane pyrrole, and tetrahydropyran; wherein the heterocycle is optionally mono- or di-substituted on carbon or nitrogen with R$_6$; optionally mono- or di-substituted on carbon with hydroxy, $-N(R_6)_2$, or $-OR_6$; optionally mono or di-substituted on carbon with the mono-valent radicals $-(C(R_6)_2)_s OR_6$ or $-[(C(R_6)_2)_s N(R_6)_2]$; or optionally mono- or di-substituted on a saturated carbon with divalent radicals =O or $-O(C(R_6)_2)_s O-$;

Ph is a phenyl ring optionally mono-, di- or tri-substituted with halogen, alkyl of 1-6 carbon atoms, trifluoromethyl, nitro, cyano, azido, halomethyl, carboxyl, alkoxycarbonyl, alkylthio, mercapto, mercaptomethyl, $-N(R_6)_2$, $-OR_6$, $-(C(R_6)_2)_s OR_6$, $-[(C(R_6)_2)_s N(R_6)_2]$, or $-(C(R_6)_2)_k Het$;

R$_6$ is hydrogen, alkyl of 1-6 carbon atoms, alkenyl of 2-6 carbon atoms, alkynyl of 2-6 carbon atoms, cycloalkyl of 1-6 carbon atoms, alkanoyl of 2-7 carbon atoms, carbamoylalkyl of 2-7 carbon atoms, hydroxyalkyl of 1-6 carbon atoms, hydroxycycloalkyl of 3-6 carbon atoms, or carboxyalkyl of 2-7 carbon atoms; or R$_6$ is phenyl optionally mono-, di-, or tri-substituted with halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, alkoxycarbonyl of 2-7 carbon atoms, phenoxy, phenyl, thiophenoxy, benzoyl, benzyl, phenylamino, benzylamino; alkanoylamino of 1-6 carbon atoms or alkyl of 1-6 carbon atoms;

R$_8$ and R$_9$ are each, independently, $-[(C(R_6)_2)_r NR_6R_6]$, or $-[(C(R_6)_2)_r OR_6]$;

J is hydrogen, chlorine, fluorine, or bromine;

L is a phenyl ring that is optionally substituted with one, two, or three substituent(s) independently selected from the group consisting of alkyl of 1-6 carbon atoms, alkenyl of 2-6 carbon atoms, alkynyl of 2-6 carbon atoms, azido, hydroxyalkyl of 1-6 carbon atoms, halogen, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, alkoxycarbonyl of 2-7 carbon atoms, alkanoyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 3-9 carbon atoms, N,N-dialkylaminoalkoxy of 4-10 carbon atoms, mercapto, methylmercapto, alkanoyloxy of 1-6 carbon atoms, alkenoyloxy of 3-8 carbon atoms, alkynoyloxy of 3-8 carbon atoms, carbamoyl, N-alkylcarbamoyl of 2-7 carbon atoms, N,N-dialkylcarbamoyl of 3-13 carbon atoms, and benzoylamino; or L is a 5- or 6-membered heteroaryl ring where the heteroaryl ring contains 1 to 3 heteroatom(s) independently selected from N, O, and S and where the heteroaryl ring may be optionally mono- or di-substituted with substituent(s) independently selected from the group consisting of halogen, oxo, thiocarbonyl, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, alkoxycarbonyl of 2-7 carbon atoms, alkanoyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 3-9 carbon atoms, N,N-dialkylaminoalkoxy of 4-10 carbon atoms, mercapto, methylmercapto, alkanoyloxy of 16 carbon atoms, alkenoyloxy of 3-8 carbon atoms, alkynoyloxy of 3-8 carbon atoms, carbamoyl, N-alkylcarbamoyl of 2-7 carbon atoms, N,N-dialkylcarbamoyl of 3-13 carbon atoms, and benzoylamino;

g=1-6;
k=0-4;
p=2-4;
q=0-4;
r=1-4;
s=1-6;
m is 0-3;

which process comprises:

(a) reacting a substituted bicyclo[4.2.0]octa-1(6),2,4-triene-7-carbonitrile of formula 1

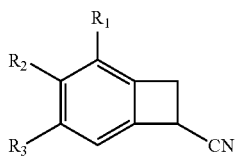

wherein $R_1$, $R_2$, and $R_3$ are defined as above;
with a base to form a first intermediate having the corresponding anion alpha to the cyano group;

(b) reacting said first intermediate with a suitable electrophilic sulfur species to yield an alpha-sulfenylated 1-cyanobenzocyclobutene of formula 2

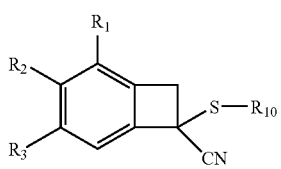

wherein $R_{10}$ is defined as an alkyl of 1-10 carbons, cycloalkyl of 3-10 carbons, alkenyl of 3-10 carbons, cycloalkenyl of 4-10 carbons, alkynyl of 3-10 carbons, Ph or L (where Ph and L are as hereinabove defined) and $R_1$, $R_2$, and $R_3$ are defined as above;

(c) reacting said cyanobenzocyclobutenes of formula 2 with an anionic salt of acetonitrile or a compound of the formula

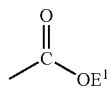

wherein $E^1$ is alkyl, phenyl, L, cycloalkyl, alkenyl, cycloalkenyl, alkynyl, any of which may be substituted with one or more $R_6$ groups; wherein L and $R_6$ are defined as above;

to provide an amino ester or intermediate of formula 3

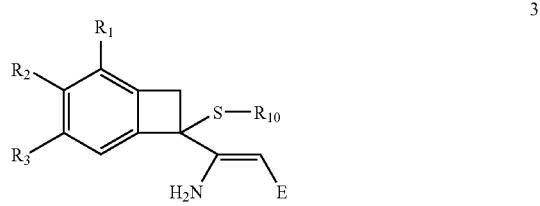

wherein $R_1$, $R_2$, $R_3$, $R_{10}$, and E are defined as above; and (d) refluxing the formula 3 adducts in a solvent to provide the substituted ester of formula A.

2. The process according to claim 1 wherein the base in step (a) is a strong base.

3. The process according to claim 1 wherein $R_{10}$ is Ph.

4. The process according to claim 1 wherein the temperature of the reaction in step (a) is a temperature of about 0° to about −100° C.

5. The process according to claim 1 wherein the reaction in step (c) is a reaction of an anionic salt of an alkyl ester or acetonitrile with said cyanobenzocyclobutene.

6. The process according to claim 1 wherein the suitable electrophilic sulfur species is an optionally substituted dialkyl disulfide or optionally substituted diphenyl disulfide.

7. The process according to claim 6 wherein the disulfide electrophile is di-p-chlorophenyl disulfide.

* * * * *